(12) United States Patent
Maruyama et al.

(10) Patent No.: US 9,181,187 B2
(45) Date of Patent: Nov. 10, 2015

(54) THERAPEUTIC AGENT FOR URINARY EXCRETION DISORDER

(75) Inventors: Takayuki Maruyama, Mishima-gun (JP); Hiroki Okada, Mishima-gun (JP); Takashi Konemura, Mishima-gun (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 12/527,340

(22) PCT Filed: Feb. 15, 2008

(86) PCT No.: PCT/JP2008/052486
§ 371 (c)(1),
(2), (4) Date: Aug. 14, 2009

(87) PCT Pub. No.: WO2008/099907
PCT Pub. Date: Aug. 21, 2008

(65) Prior Publication Data
US 2010/0076038 A1    Mar. 25, 2010

(30) Foreign Application Priority Data

Feb. 16, 2007 (JP) ................................. 2007-035661

(51) Int. Cl.
| | | |
|---|---|---|
| A61K 31/426 | (2006.01) |
| C07D 213/71 | (2006.01) |
| A61K 31/4402 | (2006.01) |
| A61K 45/06 | (2006.01) |
| C07D 277/20 | (2006.01) |
| C07D 277/36 | (2006.01) |

(52) U.S. Cl.
CPC ............ *C07D 213/71* (2013.01); *A61K 31/426* (2013.01); *A61K 31/4402* (2013.01); *A61K 45/06* (2013.01); *C07D 277/20* (2013.01); *C07D 277/36* (2013.01)

(58) Field of Classification Search
None
See application file for complete search history.

(56) References Cited

U.S. PATENT DOCUMENTS

| 7,235,667 | B2 * | 6/2007 | Naganawa et al. ........... 548/146 |
| 2005/0124672 | A1 | 6/2005 | Naganawa et al. |
| 2005/0261344 | A1 | 11/2005 | Jones et al. |

FOREIGN PATENT DOCUMENTS

| EP | 1 369 419 A1 | 12/2003 |
| EP | 2 050 446 A1 | 4/2009 |
| EP | 2050446 A1 * | 4/2009 |
| JP | 2004-099493 A | 4/2004 |
| JP | 2005-538139 A | 12/2005 |
| WO | 9315041 A1 | 8/1993 |
| WO | 9951564 A1 | 10/1999 |
| WO | 2002-072564 A1 | 9/2002 |
| WO | 2006/121097 A1 | 11/2006 |
| WO | 2008-018544 A1 | 2/2008 |
| WO | WO 2008018544 A1 * | 2/2008 |

OTHER PUBLICATIONS

Coyne K et al., The burden of lower urinary tract symptoms: evaluating the effect of LUTS on health-related quality of life, anxiety and depression: EpiLUTS, BJU International, vol. 103, issue supplement s3, (2009) 4-11.*
Robbins, Pathologic Basis of Disease, 5th ed., editors Cotran, Kumar, Robbins, Schoen, 1995, Chapter 21—The Lower Urinary Tract, p. 991-1005, at p. 996 ("Robbins").*
Kalkstein et al., Feline Idiopathic Lower Urinary Tract Disease, Part IV. Therapeutic Options, vol. 21, No. 6, Small Animal/ Exotics, Jun. 1999 ("Kalkstein").*
Parsons, Interstitial Cystitis and Lower Urinary Tract Symptoms in Males and Females—The Combined Role of Potassium and Epithelial Dysfunction, Reviews in Urology, vol. 4, Suppl. 1, 2002 ("Parsons").*
Robbins, Pathologic Basis of Disease, 5th ed., editors Cotran, Kumar, Robbins, Schoen, 1995, Chapter 21—The Lower Urinary Tract, p. 991-1005 ("Robbins").*
Greub et al "Actinobaculum massiliae," a New Species Causing Chronic Lower Urinary Tract Infection, Journal of Clinical Microbiology, Nov. 2002, vol. 40, No. 11, 3938-3941 ("Greub").*
Kalkstein et al., Feline Idiopathic Lower Urinary Tract Disease, Part IV. Therapeutic Options, vol. 21, No. 6, Small Animal/Exotics, Jun. 1999 ("Kalkstein").*
International Search Report issued for PCT/JP2008/052486 dated Apr. 22, 2009.

(Continued)

*Primary Examiner* — Svetlana M Ivanova
(74) *Attorney, Agent, or Firm* — Sughrue Mion, PLLC

(57) ABSTRACT

Disclosed is an EP1 antagonist, particularly a compound represented by the formula (I):

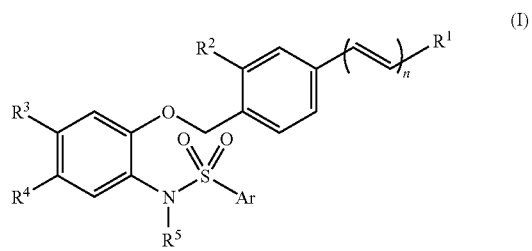

wherein all symbols are as defined in the description,
a salt thereof, a solvate thereof or a prodrug thereof. The compound, a salt thereof, a solvate thereof or a prodrug thereof is effective for prevention, treatment and/or symptom improvement of a dysuria (e.g., slow stream, splitting or spraying of the urine stream, intermittent stream, hesitancy, straining to void or terminal dribble).

5 Claims, 1 Drawing Sheet

(56) References Cited

OTHER PUBLICATIONS

Kazuki Kawabe; "A Treatment of Urination Disorder by Drugs", Gekkan Rinsho to Kenkyu; 1992, vol. 69 No. 9, pp. 2875 to 2879; ISSN: 0021-4965.

European Search Report issued on Aug. 18, 2010 in the corresponding European Patent Application No. 08711316.3.

Office Action issued on Sep. 24, 2010 from New Zealand Patent Office in the corresponding New Zealand Patent Application No. 578988.

Chinese Office Action issued on Mar. 14, 2011 in the corresponding Chinese Application No. 200880012411.5.

Ahmed et al., "Speman in Patients of Benign Prostatomegaly", Current Practice, 1983, 27(9):257-262.

Office Action issued in Canadian Patent Application No. 2677769, dated Oct. 28, 2013.

Office Action issued Jul. 2, 2013, issued by the Japanese Patent Office in corresponding Japanese Application No. 2008-558140.

Mineo Takei, "Diagnosis and Treatment of Evacuation Disorders in Women", Urogynecology Female Urology, 2005, vol. 13, No. 3; 10 pages total.

Junwu Zhang, New practical medical dictionary, Beijing Medical University, China Union Medical University, 1996, p. 1027.

Yazhou Yu, Therapeutics of Vegetative Nerve, Jilin University Press, 2006, p. 197.

Communication from the State Intellectual Property Office of the People's Republic of China, dated Aug. 7, 2013, issued in counterpart Chinese Patent Application No. 200880012411.5.

Communication from the State Intellectual Property Office of the People's Republic of China dated Nov. 11, 2013, issued in counterpart Chinese Patent Application No. 200880012411.5.

Notification of Reasons for Refusal mailed Mar. 19, 2013, issued by the Japanese Patent Office in corresponding Japanese Application No. 2008-558140.

Satoshi Seki, et al., "Urinary excretion failure practice", vol. 12, No. 4, 2004, pp. 12-17.

Takayuki Maruyama, The Japanese Journal of Urology, vol. 95, No. 2, 2004, p. 161, CP8-4.

Takayuki Doi, The Japanese Journal of Urology, vol. 95, No. 2, 2004, p. 161, CP8-5.

Abrams, et al.; "The Standardisation of Terminology of Lower Urinary Tract Function: Report from the Standardisation Sub-committee of the International Continence Society," Neurourology and Urodynamics, 2002, vol. 21; pp. 167-178.

\* cited by examiner

THERAPEUTIC AGENT FOR URINARY EXCRETION DISORDER

TECHNICAL FIELD

The present invention relates to prevention, treatment and/or symptom improvement of a dysuria by using $EP_1$ antagonist.

BACKGROUND ART

In anatomy, the "lower urinary tract" is a term referring to a route between bladder and external urethral orifice, and it has an urinary storage function of pooling urine and an excretion function of excreting urine.

According to the report of the Standardisation Sub-committee of the International Continence Society, the lower urinary tract symptoms are roughly classified into three groups: symptoms of urinary storage disorder, symptoms of dysuria and post micturition symptoms. Symptoms of urinary storage disorder are the symptoms occurring in the urinary storage phase, for example, increased daytime frequency, nocturia, urgency, urinary incontinence, enuresis and so forth are included. On the other hand, symptoms of dysuria are the symptoms occurring in the voiding phase, for example, slow stream, splitting or spraying of the urine stream, intermittent stream, hesitancy, straining to void, terminal dribble and so forth are included. Post micturition symptoms are the symptoms occurring immediately after micturition, for example, feeling of incomplete emptying, post micturition dribble and so forth are included.

Imbalance between bladder detrusor contractility and bladder outlet urethral closure pressure causes the urinary storage disorder and the dysuria. Namely, the urinary storage disorder arises from an overactive bladder (involuntary detrusor contraction), a decreased bladder outlet resistance, a reduced bladder capacity or a combination thereof. On the other hand, the dysuria arises from an impaired bladder detrusor contractility, an increased bladder outlet resistance or a combination thereof. Consequently, their pathogenic mechanisms and symptoms are distinct from each other.

Although an anticholinergic drug is used as a therapeutic agent for the urinary storage disorder (mainly, overactive bladder) at present, there is concern that it produces increased residual urine or urinary retention resulting from impaired detrusor contractility, dry mouth (depression of salivation), constipation and aggravation of cognitive disorder.

On the other hand, as a therapeutic agent for the dysuria, a medicine for increasing the force of contraction of bladder detrusor (e.g., a cholinergic drug such as bethanechol, an acetylcholinesterase inhibitor such as distigmine and so forth), or a medicine for producing relaxation of urethral smooth muscle and weakening the resistance of urethra (e.g., an α1 receptor antagonist such as tamsulosin, prazosin, alfuzosin, naftopidil, urapidil and so forth) is used. A cholinergic drug causes a bladder muscle to contract at a urinary storage phase also and impairs an urinary storage function of bladder. Moreover, it is contraindicated to pregnant woman, digestive ulcer, organic ileus, asthma and hyperthyroidism since it has side effects such as lacrimation, sweating, gastrointestinal disorder, bellyache and so forth. In view of this, satisfactory medicines have not been found out yet. An acetylcholinesterase inhibitor causes a bladder detrusor to contract whereas it causes a sphincter urethrae muscle to contract and increases the resistance of urethra due to its strong nicotinic action. A voiding efficiency is therefore deteriorated and a clinical effect is insufficient. Further, a risk of high pressure voiding is pointed out. In addition, some acetylcholinesterase inhibitors are not used in therapy since it is short-acting (Non-patent document 1). On the other hand, it is reported that an α1 receptor antagonist has the effect of improving subjective symptoms such as feeling of incomplete emptying, nocturia and so forth. However, the α1 receptor antagonist has a hypotensive effect such as orthostatic hypotension as side effect and an attention must be paid to use it for therapy.

For the meantime, EP1 involved in the present invention is one of the Prostaglandin $E_2$ (hereinafter, abbreviated as $PGE_2$) receptor subtypes of EP1, EP2, EP3 and EP4 (Non-patent document 2), and it is known that EP1 relates to diuresis (Non-patent document 3). In addition, it is known that an intravesical injection therapy of $PGE_2$ to promote urination is effective on anuretic patients (Non-patent document 4). Therefore, a compound which antagonizes to EP1, namely a EP1 antagonist is considered to be useful as a therapeutic agent of pollakiuria.

Although the relationship between EP1 antagonist and lower urinary tract diseases is disclosed in Japanese Patent No. 3741120, WO2002/15902, WO2003/43655, WO2005/00534, WO2005/10534 and WO2006/121097 on the basis of such findings, these patent documents only disclose that the EP1 antagonist is effective for prevention and treatment of "urinary storage disorder" such as pollakiuria and urinary incontinence. These patent documents neither demonstrate nor suggest substantially that the EP1 antagonist is effective for "dysuria" of which the mechanism of action and symptoms are quite different.

Moreover, the other patent documents (e.g., EP878465, WO98/27053, WO92/19617, WO96/06822, WO97/00863, WO99/47497, WO2000/20371, WO2001/19814 and WO2001/19819) which disclose the EP1 antagonist involved in the present invention do not disclose at all that the EP1 antagonist is effective for dysuria.

[Non-patent document 1] Takamichi Hattori, Kosaku Yasuda. "*Shinkeiseiboukou no Shindan to Chiryo*" 2nd edition, pp. 105-106, Igakushoin.

[Non-patent document 2] *J. Lipid Mediat. Cell Signal.*, 1995; 12: 379-391.

[Non-patent document 3] *General Pharmacology*, 1992; 23 (5): 805-809.

[Non-patent document 4] *European of Urology*, 1978; 4 (5): 366.

DISCLOSURE OF THE INVENTION

Problems to be Solved by the Invention

An agent which is safe and effective for prevention, treatment and/or symptom improvement of a dysuria is earnestly desired.

Means for Solving Problems

Since the pathogenic mechanisms of the urinary storage disorder and the dysuria are different from each other, the medication is done to each patient according to the pathogenic mechanisms. While it is reported that the EP 1 antagonist is effective for treatment of "urinary storage disorder", it has been never known at all that the EP 1 antagonist is effective for patients with "dysuria" who show the contradictory symptoms. If a medicine characterized in single EP 1 antagonist activity is effective for all patients with lower urinary tract diseases, such medicine can be developed economically and expeditiously. In addition, comprehensive remedy for lower urinary tract diseases is useful for doctors and patients.

The inventors of the present invention have conducted intensive studies in view of such circumstances and found that the EP1 antagonist involved in the present invention increases urinary flow rate which is a objective finding to evaluate voiding and decreases residual urine rate. Through these findings, the inventors have found that the EP1 antagonist is effective for prevention, treatment and/or symptom improvement of a dysuria and thereby accomplished the present invention.

Namely, the present invention relates to (1) an agent for prevention, treatment and/or symptom improvement of a dysuria comprising a compound represented by the formula (I):

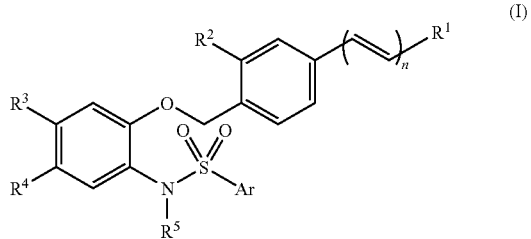

in which all symbols have the same meanings as described below, a salt thereof, a solvate thereof or a prodrug thereof;

(2) the agent according to above (1), wherein the compound represented by the formula (I) is 3-methyl-4-[6-[N-isobutyl-N-(2-thiazolylsulfonyl)amino]indan-5-yloxymethyl]benzoic acid or 4-[6-[N-isobutyl-N-(4-methyl-2-thiazolylsulfonyl)amino]indan-5-yloxymethyl]benzoic acid;

(3) the agent according to above (1), wherein the symptom of the dysuria is slow stream, splitting or spraying of the urine stream, intermittent stream, hesitancy, straining to void and/or terminal dribble;

(4) the agent according to above (1), which has the contractile action on detrusor muscle and the weakening action on bladder outlet resistance;

(5) the agent according to above (1), which increases urinary flow rate and/or decreases residual urine rate;

(6) a medicament comprising a combination of a compound represented by the formula (I), a salt thereof, a solvate thereof or a prodrug thereof and an α1 receptor antagonist and/or an acetylcholinesterase inhibitor;

(7) a method for prevention, treatment and/or symptom improvement of a dysuria, which comprises administering an effective amount of a compound represented by the formula (I), a salt thereof, a solvate thereof or a prodrug thereof to a mammal; and (8) use of a compound represented by the formula (I), a salt thereof, a solvate thereof or a prodrug thereof for the manufacture of an agent for prevention, treatment and/or symptom improvement of a dysuria.

Effect of the Invention

The EP 1 antagonist involved in the present invention is effective for prevention, treatment and/or symptom improvement of a dysuria (e.g., slow stream, splitting or spraying of the urine stream, intermittent stream, hesitancy, straining to void, terminal dribbling and so forth), since it increases urinary flow rate and decreases residual urine rate through the contractile action on detrusor muscle and the weakening action on bladder outlet resistance.

BEST MODE FOR CARRYING OUT THE INVENTION

In the description of the present invention, the $EP_1$ antagonist includes the following compounds, for example, a compound represented by the formula (A) disclosed in Japanese Patent No. 3426252:

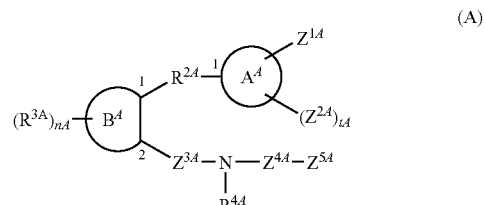

wherein the group

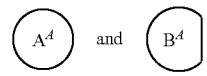

each independently represents a C5-15 carbocyclic ring or a 5-7 membered heterocyclic ring containing one or two oxygen, sulfur or nitrogen atoms;

$Z^{1A}$ represents a group represented by —$COR^{1A}$, —C1-4 alkylene-$COR^{1A}$, —CH=CH—$COR^{1A}$, —C≡C—$COR^{1A}$, —O—C1-3 alkylene-$COR^{1A}$ (wherein $R^{1A}$ represents hydroxy, C1-6 alkoxy or a group represented by formula —$NR^{6A}R^{7A}$ (wherein $R^{6A}$ and $R^{7A}$ each independently represent a hydrogen atom or C1-4 alkyl)) or —C1-5 alkylene-OH;

$Z^{2A}$ represents a hydrogen atom, C1-4 alkyl, C1-4 alkoxy, nitro, halogen, trifluoromethyl, trifluoromethoxy, hydroxy or a group represented by formula —$COR^{1A}$ (wherein $R^{1A}$ has the same meaning as described above);

$Z^{3A}$ represents a single bond or C1-4 alkylene;

$Z^{4A}$ represents $SO_2$ or CO;

$Z^{5A}$ represents (1) C1-8 alkyl, C2-8 alkenyl or C2-8 alkynyl, (2) phenyl, C3-7 cycloalkyl, a 5-7 membered heterocyclic ring containing one or two oxygen, sulfur or nitrogen atoms, or (3) C1-4 alkyl, C2-4 alkenyl or C2-4 alkynyl substituted by phenyl or C3-7 cycloalkyl, wherein phenyl, C3-7 cycloalkyl and a 5-7 membered heterocyclic ring containing one or two oxygen, sulfur or nitrogen atoms in above-described (2) and (3) may be substituted by 1-5$R^{5A}$ group (more than one $R^{5A}$ independently represents a hydrogen atom, C1-6 alkyl, C1-6 alkoxy, C1-6 alkylthio, nitro, halogen, trifluoromethyl, trifluoromethoxy or hydroxy);

$R^{2A}$ represents —$CONR^{8A}$—, —$NR^{8A}CO$—, —$CONR^{8A}$—C1-4 alkylene-, —C1-4 alkylene-$CONR^{8A}$—, —$NR^{8A}CO$—C1-4 alkylene-, —C1-4 alkylene-$NR^{8A}CO$—, —C1-3 alkylene-$CONR^{8A}$—C1-3 alkylene-, —C1-3 alkylene-$NR^{8A}CO$—C1-3 alkylene- (wherein $R^{8A}$ represents a hydrogen atom or C1-4 alkyl), O, S, a group represented by —$NZ^{6A}$- (wherein $Z^{6A}$ represents a hydrogen atom or C1-4 alkyl), —$Z^{7A}$—C1-4 alkylene-, —C1-4 alkylene-$Z^{7A}$—, —C1-3 alkylene-$Z^{7A}$—C1-3 alkylene- (wherein $Z^{7A}$ represents O, S or $NZ^{6A}$ (wherein $Z^{6A}$ has the same meaning as described above)), —CO—, —CO—C1-4 alkylene-, —C1-4 alkylene-CO—, —C1-3 alkylene-CO—C1-3 alkylene-, —C2-4 alkylene, C2-4 alkenylene or C2-4 alkynylene;

$R^{3A}$ represents a hydrogen atom, C1-6 alkyl, C1-6 alkoxy, C1-6 alkylthio, nitoro, halogen, trifluoromethyl, trifluoromethoxy, hydroxy or hydroxymethyl;

$R^{4A}$ represents (1) a hydrogen atom, (2) C1-8 alkyl, C2-8 alkenyl or C2-8 alkynyl, (3) C1-6 alkyl substituted by one or two group(s) selected from the group consisting of $COOZ^{8A}$, $CONZ^{9A}Z^{10A}$, $OZ^{8A}$, (wherein, $Z^{8A}$, $Z^{9A}$ and $Z^{10A}$ independently represent a hydrogen atom or C1-4 alkyl) and C1-4 alkoxy-C1-4 alkoxy, (4) C3-7 cycloalkyl or (5) C1-4 alkyl, C2-4 alkenyl or C2-4 alkynyl substituted by phenyl or C3-7 cycloalkyl (phenyl or C3-7 cycloalkyl in above-described (4) and (5) may be substituted by 1-5$R^{5A}$ group(s) ($R^{5A}$ has the same meaning as described above));

nA and tA each independently represents an integer from 1 to 4;

wherein $R^{2A}$ and $Z^{3A}$ each independently only binds to the 1- or 2-position of

and $Z^{1A}$ only binds to the 3 or 4-position of a benzene ring in cases where

represents the benzene ring and $(Z^{2A})_{tA}$ represents other than $COR^{1A}$ (details of the definition of symbols of formula correspond to those described in the patent specification), an alkyl ester thereof, a salt thereof a solvate thereof or a prodrug thereof;

a compound represented by the formula (B) described in EP878465:

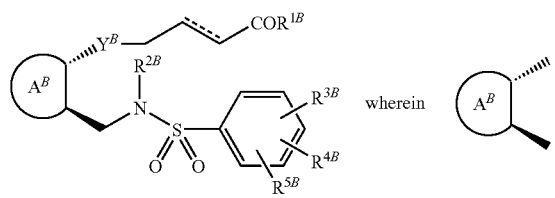

wherein $A^B$ represents a group represented by formula

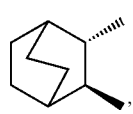  (a)

(b)

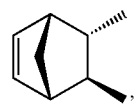  (c)

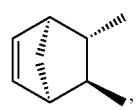  (d)

  (e)

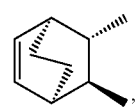  (f)

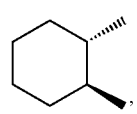  (g)

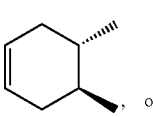  (h)

, or

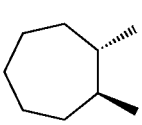  (i)

;

$R^{1B}$ represents hydroxy, C1-4 alkoxy or a group represented by formula $NR^{6B}R^{7B}$ (wherein $R^{6B}$ and $R^{7B}$ each independently represents a hydrogen atom or C1-4 alkyl);

$R^{2B}$ represents a hydrogen atom or C1-4 alkyl;

$R^{3B}$ and $R^{4B}$ each independently represent C1-4 alkyl, a halogen atom or trifluoromethyl;

$R^{5B}$ represents a hydrogen atom, C1-4 alkyl, a halogen atom or trifluoromethyl;

$Y^B$ represents cis-vinylene or trans-vinylene;

symbol ⟿
represents a single bond or double bond;
wherein

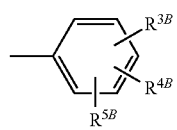

does not represent

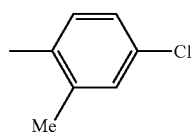

in cases where

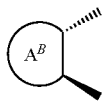

represents formula

$R^{1B}$ represents hydroxy or C1-4 alkoxy; $R^{2B}$ represents a hydrogen atom; $Y^B$ represents cis-vinylene; and symbol ⁓ represents a single bond (details of the definition of symbols of formula correspond to those described in the patent specification), a salt thereof, a solvate thereof or a prodrug thereof;

a compound represented by the formula (E) described in WO2006/121097:

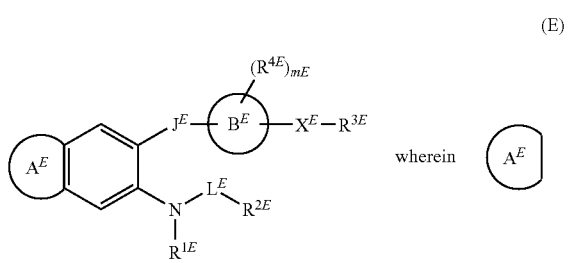

represents optionally substituted 5-8 membered heterocyclic ring;

represents cycloalkyl, a benzene ring, or a heterocyclic ring;

$R^{1E}$ represents lower alkyl or a heterocyclic ring, each of which is optionally substituted;

$R^{2E}$ represents C1-12 alkyl, cycloalkyl, aryl, a heterocyclic ring, -lower alkylene-cycloalkyl, -lower alkylene-aryl or -lower alkylene-heterocyclic ring wherein C1-12 alkyl, cycloalkyl, aryl and a heterocyclic ring in $R^{2E}$ may be substituted;

$R^{3E}$ represents —OH, —C(O)—$R^{OE}$, —C(O)—$NR^{5E}R^{5aE}$, 1H-tetrazol-5-yl or 5-oxo-4,5-dihydro-1,2,4-oxadiazol-3-yl;

$R^{OE}$ and $R^{OOE}$ are same or different and represent a hydrogen atom or lower alkyl;

$R^{5E}$ and $R^{5aE}$ are same or different and represent —$R^{OE}$, -lower alkylene-$NR^{OE}R^{OOE}$, -lower alkylene-$COR^{OE}$, cycloalkyl, aryl, heterocyclic ring, -lower alkylene-cycloalkyl, -lower alkylene-aryl, -lower alkylene-heterocyclic ring, —$SO_2$-lower alkyl, —$SO_2$-lower alkylene-$OR^{OE}$ or —$SO_2$-lower alkylene-O—C(O)— lower alkyl wherein cycloalkyl, aryl and a heterocyclic ring in $R^{5E}$ and $R^{5aE}$ may be substituted;

$R^{4E}$ represents halogen, lower alkyl, halogeno-lower alkyl, cyano, nitro, —$OR^{OE}$, —O-halogeno-lower alkyl, —C(O)$R^{OE}$ or —$NR^{OE}C(O)R^{OOE}$;

$m^E$ is 0, one or two wherein two $R^{4E}$ may be same or different to each other in cases where $m^E$ is two;

$J^E$ represents lower alkylene, lower alkenylene, —O-lower alkylene-, -lower alkylene-O—, —O-lower alkenylene, -lower alkenylene-O—, —C(O)$NR^{OE}$ or —$NR^{OE}C(O)$—;

$X^E$ represents a single bond, lower alkylene, lower alkenylene, —O-lower alkylene-, —O-lower alkenylene-, —$NR^{OE}$-lower alkylene-, —$S(O)_{nE}$-lower alkylene- or —$S(O)_{nE}$-lower alkenylene-;

$N^E$ is 0, one or two;

$L^E$ represents a single bond, —C(O)— or —$S(O)_2$— (details of the definition of symbols of formula correspond to those described in the patent specification), an alkyl ester thereof, a salt thereof, a solvate thereof or a prodrug thereof;

a compound represented by the formula (G) described in WO 2007/072782:

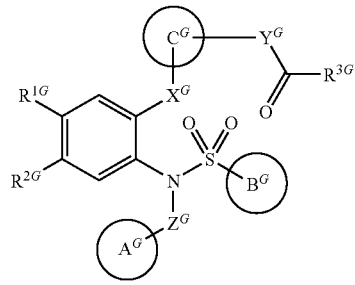

wherein $R^{1G}$ and $R^{2G}$ are same or different and represent a hydrogen atom, halogen, lower alkyl, halogeno-lower alkyl, —OH, —O-lower alkyl or $R^{1G}$ and $R^{2G}$ may form a 5-8 membered cycloalkene ring or a benzene ring together with the carbon to which they bind;

$R^{3G}$ represents —OH, —O-lower alkyl or —NH—$SO_2$—(lower alkyl which may be substituted by the groups selected from —OH and —O—C(=O)-lower alkyl);

$A^G$ represents an optionally substituted heterocyclic ring;

$B^G$ represents an optionally substituted phenyl or an optionally substituted monocyclic heteroaryl;

$C^G$ represents an optionally substituted phenylene or an optionally substituted monocyclic heteroarylene;

$X^G$ represents lower alkylene, lower alkenylene, —O-lower alkylene or -lower alkylene-O—;

$Y^G$ represents a single bond, lower alkylene, lower alkenylene, or —O-lower alkylene;

$Z^G$ represents lower alkylene (details of the definition of symbols of formula correspond to those described in the patent specification), an alkyl ester thereof, a salt thereof, a solvate thereof or a prodrug thereof; and a compound represented by the formula (I) described in Japanese Patent No. 3741120:

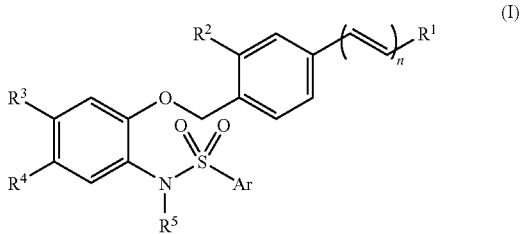

(I)

wherein $R^1$ represents —COOR$^{1-1}$ (wherein $R^{1-1}$ represents a hydrogen atom or C1-6 alkyl), 5-tetrazolyl, 5-oxo-1,2,4-oxadiazolyl, —CH$_2$OH or 5-oxo-1,2,4-thiadiazolyl;

$R^2$ represents a hydrogen atom, methyl, methoxy or chloro;

$R^3$ and $R^4$ represent a combination of (1) methyl and methyl, (2) methyl and chloro, (3) chloro and methyl or (4) trifluoromethyl and a hydrogen atom, or $R^3$ and $R^4$ form (5) cyclopentene, (6) cyclohexene or (7) a benzene ring together with the carbon atom to which they bind;

$R^5$ represents isopropyl, isobutyl, 2-methyl-2-propenyl, cyclopropylmethyl, methyl, ethyl, propyl or 2-hydroxy-2-methylpropyl;

Ar represents thiazolyl optionally substituted by methyl residue, pyridyl or 5-methyl-2-furyl;

n is 0 or 1; wherein n is 0 in cases where $R^1$ is 5-tetrazolyl, 5-oxo-1,2,4-oxadiazolyl or 5-oxo-1,2,4-thiadiazolyl, a salt thereof, a solvate thereof or a prodrug thereof.

In the present invention, C1-6 alkyl of $R^{1-1}$ in the formula (I) specifically includes methyl, ethyl, n-propyl, isopropyl, n-butyl, isobutyl, sec-butyl, tert-butyl, n-pentyl, n-hexyl and so forth.

In the present invention, Ar in the formula (I) is preferably 5-methyl-2-furyl, 2-thiazolyl, 5-methyl-2-thiazolyl, 2-pyridyl or 3-pyridyl, $R^1$ is preferably —COOR$^{1-1}$ and $R^{1-1}$ is preferably a hydrogen atom.

In the present invention, the preferable compounds of the formula (I) are the following compounds: namely, (1) 4-[2-[N-isobutyl-N-(5-methyl-2-furylsulfonyl)amino]-5-trifluoromethylphenoxymethyl]cinnamic acid,
(2) 4-[2-[N-isopropyl-N-(5-methyl-2-furylsulfonyl)amino]-5-trifluoromethylphenoxymethyl]benzoic acid,
(3) 4-[2-[N-isobutyl-N-(5-methyl-2-furylsulfonyl)amino]-5-trifluoromethylphenoxymethyl]benzoic acid,
(4) 4-[2-[N-isobutyl-N-(5-methyl-2-furylsulfonyl)amino]-4-chloro-5-methylphenoxymethyl]benzoic acid,
(5) 4-[2-[N-isopropyl-N-(5-methyl-2-furylsulfonyl)amino]-4,5-dimethylphenoxymethyl]benzoic acid,
(6) 4-[2-[N-isobutyl-N-(5-methyl-2-furylsulfonyl)amino]-4,5-dimethylphenoxymethyl]benzoic acid (hereafter, abbreviated as compound D),
(7) 3-methyl-4-[2-[N-isobutyl-N-(5-methyl-2-furylsulfonyl)amino]-4-methyl-5-chlorophenoxymethyl]benzoic acid,
(8) 3-methyl-4-[2-[N-isobutyl-N-(5-methyl-2-furylsulfonyl)amino]-4-chloro-5-methylphenoxymethyl]benzoic acid,
(9) 3-chloro-4-[2-[N-isobutyl-N-(5-methyl-2-furylsulfonyl)amino]-4-methyl-5-chlorophenoxymethyl]benzoic acid,
(10) 3-chloro-4-[2-[N-isopropyl-N-(5-methyl-2-furylsulfonyl)amino]-4-methyl-5-chlorophenoxymethyl]benzoic acid,
(11) 3-methoxy-4-[2-[N-isopropyl-N-(5-methyl-2-furylsulfonyl)amino]-4-methyl-5-chlorophenoxymethyl]benzoic acid,
(12) 3-methyl-4-[2-[N-isobutyl-N-(5-methyl-2-furylsulfonyl)amino]-4,5-dimethylphenoxymethyl]benzoic acid (hereafter, abbreviated as compound C),
(13) 3-methoxy-4-[2-[N-isopropyl-N-(5-methyl-2-furylsulfonyl)amino]-4,5-dimethylphenoxymethyl]benzoic acid,
(14) 3-methoxy-4-[2-[N-isobutyl-N-(5-methyl-2-furylsulfonyl)amino]-4,5-dimethylphenoxymethyl]benzoic acid,
(15) 3-methoxy-4-[2-[N-isopropyl-N-(5-methyl-2-furylsulfonyl)amino]-4-chloro-5-methylphenoxymethyl]benzoic acid,
(16) 3-chloro-4-[2-[N-isobutyl-N-(5-methyl-2-furylsulfonyl)amino]-4,5-dimethylphenoxymethyl]benzoic acid,
(17) 3-chloro-4-[2-[N-isopropyl-N-(5-methyl-2-furylsulfonyl)amino]-4,5-dimethylphenoxymethyl]benzoic acid,
(18) 3-methyl-4-[2-[N-isobutyl-N-(5-methyl-2-furylsulfonyl)amino]-4-chloro-5-methylphenoxymethyl]cinnamic acid,
(19) 4-[2-[N-isopropyl-N-(5-methyl-2-furylsulfonyl)amino]-4-methyl-5-chlorophenoxymethyl]cinnamic acid,
(20) 4-[2-[N-isobutyl-N-(5-methyl-2-furylsulfonyl)amino]-4-methyl-5-chlorophenoxymethyl]cinnamic acid,
(21) 4-[2-[N-isopropyl-N-(5-methyl-2-furylsulfonyl)amino]-4,5-dimethylphenoxymethyl]cinnamic acid,
(22) 3-methyl-4-[2-[N-isopropyl-N-(5-methyl-2-furylsulfonyl)amino]-5-trifluoromethylphenoxymethyl]cinnamic acid,
(23) 3-methyl-4-[2-[N-isopropyl-N-(5-methyl-2-furylsulfonyl)amino]-4,5-dimethylphenoxymethyl]benzoic acid,
(24) 3-methyl-4-[2-[N-isopropyl-N-(5-methyl-2-furylsulfonyl)amino]-4,5-dimethylphenoxymethyl]cinnamic acid,
(25) 3-methyl-4-[2-[N-isobutyl-N-(5-methyl-2-furylsulfonyl)amino]-4,5-dimethylphenoxymethyl]cinnamic acid,
(26) 4-[2-[N-isobutyl-N-(5-methyl-2-furylsulfonyl)amino]-4,5-dimethylphenoxymethyl]cinnamic acid,
(27) N-[4-chloro-5-methyl-2-[2-methyl-4-(5-tetrazolyl)phenylmethyloxy]phenyl]-N-isobutyl-(5-methyl-2-furyl)sulfonylamide,
(28) 3-methoxy-4-[2-[N-isobutyl-N-(5-methyl-2-furylsulfonyl)amino]-4-methyl-5-chlorophenoxymethyl]cinnamic acid,
(29) N-[4,5-dimethyl-2-[2-methyl-4-(5-tetrazolyl)phenylmethyloxy]phenyl]-N-isobutyl-(5-methyl-2-furyl)sulfonylamide,
(30) N-[4,5-dimethyl-2-[2-methyl-4-(5-tetrazolyl)phenylmethyloxy]phenyl]-N-isopropyl-(5-methyl-2-furyl)sulfonylamide,
(31) N-[4-chloro-5-methyl-2-[4-(5-tetrazolyl)phenylmethyloxy]phenyl]-N-isobutyl-(5-methyl-2-furyl)sulfonylamide,
(32) N-[4-chloro-5-methyl-2-[4-(5-oxo-1,2,4-oxadiazol-3-yl-1,2,4-oxadiazol-3-yl)phenylmethyloxy]phenyl]-N-isopropyl-(5-methyl-2-furyl)sulfonylamide
(33) N-[4-chloro-5-methyl-2-[4-(5-oxo-1,2,4-oxadiazol-3-yl)phenylmethyloxy]phenyl]-N-isobutyl-(5-methyl-2-furyl)sulfonylamide,
(34) 4-[6-[N-isobutyl-N-(5-methyl-2-furylsulfonyl)amino]indan-5-yloxymethyl]benzoic acid,
(35) 4-[6-[N-isopropyl-N-(5-methyl-2-furylsulfonyl)amino]indan-5-yloxymethyl]benzoic acid,
(36) 4-[7-[N-isobutyl-N-(5-methyl-2-furylsulfonyl)amino]-1,2,3,4-tetrahydronaphtharen-6-yloxymethyl]benzoic acid,
(37) 4-[7-[N-isopropyl-N-(5-methyl-2-furylsulfonyl)amino]-1,2,3,4-tetrahydronaphtharen-6-yloxymethyl]benzoic acid,

(38) N-[4,5-dimethyl-2-[2-methyl-4-(5-oxo-1,2,4-oxadiazol-3-yl)phenylmethyloxy]phenyl]-N-isopropyl-(5-methyl-2-furyl)sulfonylamide,
(39) N-[4,5-dimethyl-2-[2-methyl-4-(5-oxo-1,2,4-oxadiazol-3-yl)phenylmethyloxy]phenyl]-N-isobutyl-(5-methyl-2-furyl)sulfonylamide,
(40) N-[4,5-dimethyl-2-[4-(5-tetrazolyl)phenylmethyloxy]phenyl]-N-isopropyl-(5-methyl-2-furyl)sulfonylamide,
(41) N-[4,5-dimethyl-2-[4-(5-tetrazolyl)phenylmethyloxy]phenyl]-N-isobutyl-(5-methyl-2-furyl)sulfonylamide,
(42) N-[4,5-dimethyl-2-[4-(5-oxo-1,2,4-oxadiazol-3-yl)phenylmethyloxy]phenyl]-N-isobutyl-(5-methyl-2-furyl)sulfonylamide,
(43) 3-methyl-4-[2-[N-isobutyl-N-(5-methyl-2-furylsulfonyl)amino]-4-methyl-5-chlorophenoxymethyl]cinnamic acid,
(44) N-[4,5-dimethyl-2-[2-methoxy-4-(5-oxo-1,2,4-oxadiazol-3-yl)phenylmethyloxy]phenyl]-N-isobutyl-(5-methyl-2-furyl)sulfonylamide,
(45) N-[4,5-dimethyl-2-[2-methoxy-4-(5-oxo-1,2,4-oxadiazol-3-yl)phenylmethyloxy]phenyl]-N-isopropyl-(5-methyl-2-furyl)sulfonylamide,
(46) 4-[6-[N-isobutyl-N-(5-methyl-2-furylsulfonyl)amino]indan-5-yloxymethyl]cinnamic acid (hereafter, abbreviated as compound E),
(47) 3-methyl-4-[6-[N-isobutyl-N-(5-methyl-2-furylsulfonyl)amino]indan-5-yloxymethyl]benzoic acid (hereafter, abbreviated as compound F),
(48) 3-methyl-4-[6-[N-isobutyl-N-(5-methyl-2-furylsulfonyl)amino]indan-5-yloxymethyl]cinnamic acid,
(49) 4-[2-[N-(2-methyl-2-propenyl)-N-(5-methyl-2-furylsulfonyl)amino]-4,5-dimethylphenoxymethyl]benzoic acid,
(50) 3-methyl-4-[6-[N-isopropyl-N-(5-methyl-2-furylsulfonyl)amino]indan-5-yloxymethyl]benzoic acid,
(51) 3-methyl-4-[6-[N-isopropyl-N-(5-methyl-2-furylsulfonyl)amino]indan-5-yloxymethyl]cinnamic acid,
(52) 4-[6-[N-isopropyl-N-(5-methyl-2-furylsulfonyl)amino]indan-5-yloxymethyl]cinnamic acid,
(53) 4-[3-[N-isobutyl-N-(5-methyl-2-furylsulfonyl)amino]-2-naphthyloxymethyl]benzoic acid,
(54) 3,5-dimethyl-4-[2-[N-isobutyl-N-(5-methyl-2-furylsulfonyl)amino]-5-trifluoromethylphenoxymethyl]benzoic acid,
(55) 3-methyl-4-[6-[N-(2-methyl-2-propenyl)-N-(5-methyl-2-furylsulfonyl)amino]indan-5-yloxymethyl]benzoic acid,
(56) 4-[6-[N-cyclopropylmethyl-N-(5-methyl-2-furylsulfonyl)amino]indan-5-yloxymethyl]-3-methylbenzoic acid,
(57) 4-[6-[N-isobutyl-N-(5-methyl-2-furylsulfonyl)amino]indan-5-yloxymethyl]-3-methylbenzylalcohol,
(58) 3-methyl-4-[6-[N-methyl-N-(5-methyl-2-furylsulfonyl)amino]indan-5-yloxymethyl]benzoic acid,
(59) 4-[6-[N-ethyl-N-(5-methyl-2-furylsulfonyl)amino]indan-5-yloxymethyl]-3-methylbenzoic acid,
(60) 4-[6-[N-methyl-N-(5-methyl-2-furylsulfonyl)amino]indan-5-yloxymethyl]cinnamic acid,
(61) 4-[6-[N-ethyl-N-(5-methyl-2-furylsulfonyl)amino]indan-5-yloxymethyl]cinnamic acid,
(62) 4-[6-[N-propyl-N-(5-methyl-2-furylsulfonyl)amino]indan-5-yloxymethyl]cinnamic acid,
(63) 4-[4,5-dimethyl-2-[N-(2-methyl-2-propenyl)-N-(5-methyl-2-furylsulfonyl)amino]phenoxymethyl]-3-methylbenzoic acid,
(64) 4-[6-[N-(2-methyl-2-propenyl)-N-(5-methyl-2-furylsulfonyl)amino]indan-5-yloxymethyl]cinnamic acid,
(65) 4-[6-[N-cyclopropylmethyl-N-(5-methyl-2-furylsulfonyl)amino]indan-5-yloxymethyl]cinnamic acid,
(66) 4-[6-[N-(2-propenyl)-N-(5-methyl-2-furylsulfonyl)amino]indan-5-yloxymethyl]cinnamic acid,
(67) 3-methyl-4-[6-[N-propyl-N-(5-methyl-2-furylsulfonyl)amino]indan-5-yloxymethyl]benzoic acid,
(68) 3-methyl-4-[6-[N-(2-propenyl)-N-(5-methyl-2-furylsulfonyl)amino]indan-5-yloxymethyl]benzoic acid,
(69) 4-[4,5-dimethyl-2-[N-methyl-N-(5-methyl-2-furylsulfonyl)amino]phenoxymethyl]benzoic acid,
(70) 4-[4,5-dimethyl-2-[N-ethyl-N-(5-methyl-2-furylsulfonyl)amino]phenoxymethyl]benzoic acid,
(71) 4-[4,5-dimethyl-2-[N-(5-methyl-2-furylsulfonyl)-N-propylamino]phenoxymethyl]benzoic acid,
(72) 4-[3-[N-isopropyl-N-(5-methyl-2-furylsulfonyl)amino]naphtharen-2-yloxymethyl]-3-methylbenzoic acid,
(73) 4-[3-[N-isobutyl-N-(5-methyl-2-furylsulfonyl)amino]naphtharen-2-yloxymethyl]-3-methylbenzoic acid,
(74) 4-[3-[N-isopropyl-N-(5-methyl-2-furylsulfonyl)amino]naphtharen-2-yloxymethyl]cinnamic acid,
(75) 4-[3-[N-isobutyl-N-(5-methyl-2-furylsulfonyl)amino]naphtharen-2-yloxymethyl]cinnamic acid,
(76) 3-methyl-4-[3-[N-isopropyl-N-(5-methyl-2-furylsulfonyl)amino]naphtharen-2-yloxymethyl]cinnamic acid,
(77) 3-methyl-4-[3-[N-isobutyl-N-(5-methyl-2-furylsulfonyl)amino]naphtharen-2-yloxymethyl]cinnamic acid,
(78) 4-[4,5-dimethyl-2-[N-[(5-methyl-2-furylsulfonyl]-N-2-propenylamino]phenoxymethyl]benzoic acid,
(79) 4-[4,5-dimethyl-2-[N-methyl-N-(5-methyl-2-furylsulfonyl)amino]phenoxymethyl]-3-methylbenzoic acid,
(80) 4-[4,5-dimethyl-2-[N-ethyl-N-(5-methyl-2-furylsulfonyl)amino]phenoxymethyl]-3-methylbenzoic acid,
(81) 4-[4,5-dimethyl-2-[N-(5-methyl-2-furylsulfonyl)-N-propylamino]phenoxymethyl]-3-methylbenzoic acid,
(82) 4-[4,5-dimethyl-2-[N-(5-methyl-2-furylsulfonyl)-N-(2-propenylamino]phenoxymethyl]-3-methylbenzoic acid,
(83) 4-[4,5-dimethyl-2-[N-(2-hydroxy-2-methylpropyl)-N-(5-methyl-2-furylsulfonyl)amino]phenoxymethyl]-3-methylbenzoic acid,
(84) 4-[6-[N-(2-hydroxy-2-methylpropyl)-N-(5-methyl-2-furylsulfonyl)amino]indan-5-yloxymethyl]-3-methylbenzoic acid,
(85) 4-[4,5-dimethyl-2-[N-cyclopropylmethyl-N-(5-methyl-2-furylsulfonyl)amino]phenoxymethyl]benzoic acid,
(86) 4-[4,5-dimethyl-2-[N-(2-hydroxy-2-methylpropyl)-N-(5-methyl-2-furylsulfonyl)amino]phenoxymethyl]benzoic acid,
(87) 4-[6-[N-(2-hydroxy-2-methylpropyl)-N-(5-methyl-2-furylsulfonyl)amino]indan-5-yloxymethyl]cinnamic acid,
(88) 4-[4,5-dimethyl-2-[N-cyclopropylmethyl-N-(5-methyl-2-furylsulfonyl)amino]phenoxymethyl]-3-methylbenzoic acid,
(89) 4-[2-[N-isopropyl-N-(2-thiazolylsulfonyl)amino]-5-trifluoromethylphenoxymethyl]benzoic acid,
(90) 4-[2-[N-isobutyl-N-(2-thiazolylsulfonyl)amino]-5-trifluoromethylphenoxymethyl]benzoic acid,
(91) 4-[2-[N-isopropyl-N-(2-thiazolylsulfonyl)amino]-5-trifluoromethylphenoxymethyl]cinnamic acid,
(92) 4-[2-[N-isobutyl-N-(2-thiazolylsulfonyl)amino]-5-trifluoromethylphenoxymethyl]cinnamic acid,
(93) 4-[2-[N-isobutyl-N-(4-methyl-2-thiazolylsulfonyl)amino]-5-trifluoromethylphenoxymethyl]benzoic acid,
(94) 4-[2-[N-isobutyl-N-(4-methyl-2-thiazolylsulfonyl)amino]-5-trifluoromethylphenoxymethyl]cinnamic acid (hereafter, abbreviated as compound G),
(95) 4-[2-[N-isopropyl-N-(2-thiazolylsulfonyl)amino]-4-chloro-5-methylphenoxymethyl]benzoic acid,

(96) N-[4-trifluoromethyl-2-[4-(5-tetrazolyl)phenylmethyloxy]phenyl]-N-isobutyl-2-thiazolylsulfonylamide,
(97) N-[4-trifluoromethyl-2-[4-(5-tetrazolyl)phenylmethyloxy]phenyl]-N-isopropyl-2-thiazolylsulfonylamide,
(98) N-[4-trifluoromethyl-2-[4-(5-oxo-1,2,4-oxadiazol-3-yl)phenylmethyloxy]phenyl]-N-isopropyl-2-thiazolylsulfonylamide,
(99) N-[4-trifluoromethyl-2-[4-(5-oxo-1,2,4-thiadiazol-3-yl-1,2,4-thiadiazol-3-yl)phenylmethyloxy]phenyl]-N-isopropyl-2-thiazolylsulfonylamide
(100) 4-[2-[N-isopropyl-N-(4-methyl-2-thiazolylsulfonyl)amino]-4-chloro-5-methylphenoxymethyl]benzoic acid,
(101) 4-[2-[N-isobutyl-N-(4-methyl-2-thiazolylsulfonyl)amino]-4-chloro-5-methylphenoxymethyl]benzoic acid,
(102) 3-chloro-4-[2-[N-isopropyl-N-(4-methyl-2-thiazolylsulfonyl)amino]-4-chloro-5-methylphenoxymethyl]benzoic acid,
(103) 3-methyl-4-[2-[N-isobutyl-N-(4-methyl-2-thiazolylsulfonyl)amino]-5-trifluoromethylphenoxymethyl]benzoic acid,
(104) 3-methyl-4-[2-[N-isobutyl-N-(4-methyl-2-thiazolylsulfonyl)amino]-4-chloro-5-methylphenoxymethyl]benzoic acid,
(105) 3-methoxy-4-[2-[N-isobutyl-N-(4-methyl-2-thiazolylsulfonyl)amino]-4-chloro-5-methylphenoxymethyl]benzoic acid,
(106) 3-methoxy-4-[2-[N-isobutyl-N-(4-methyl-2-thiazolylsulfonyl)amino]-5-trifluoromethylphenoxymethyl]benzoic acid,
(107) N-[4-trifluoromethyl-2-[4-(5-tetrazolyl)phenylmethyloxy]phenyl]-isobutyl-(4-methyl-2-thiazolyl)sulfonylamide,
(108) N-[4-trifluoromethyl-2-[4-(5-oxo-1,2,4-oxadiazol-3-yl)phenylmethyloxy]phenyl]-N-isopropyl-(4-methyl-2-thiazolyl)sulfonylamide,
(109) N-[4-trifluoromethyl-2-[4-(5-oxo-1,2,4-oxadiazol-3-yl)phenylmethyloxy]phenyl]-N-isobutyl-(4-methyl-2-thiazolyl)sulfonylamide,
(110) 4-[2-[N-isobutyl-N-(4-methyl-2-thiazolylsulfonyl)amino]-4-methyl-5-chlorophenoxymethyl]benzoic acid,
(111) 3-chloro-4-[2-[N-isobutyl-N-(4-methyl-2-thiazolylsulfonyl)amino]-4-methyl-5-chlorophenoxymethyl]benzoic acid,
(112) 3-methoxy-4-[2-[N-isobutyl-N-(4-methyl-2-thiazolylsulfonyl)amino]-4-methyl-5-chlorophenoxymethyl]benzoic acid,
(113) N-[4-trifluoromethyl-2-[4-(5-tetrazolyl)phenylmethyloxy]phenyl]-N-isopropyl-(4-methyl-2-thiazolyl)sulfonylamide,
(114) 3-methyl-4-[2-[N-isobutyl-N-(4-methyl-2-thiazolylsulfonyl)amino]-4,5-dimethylphenoxymethyl]benzoic acid,
(115) 3-methyl-4-[2-[N-isopropyl-N-(4-methyl-2-thiazolylsulfonyl)amino]-4,5-dimethylphenoxymethyl]benzoic acid,
(116) 3-methoxy-4-[2-[N-isobutyl-N-(4-methyl-2-thiazolylsulfonyl)amino]-4,5-dimethylphenoxymethyl]benzoic acid,
(117) 3-chloro-4-[2-[N-isobutyl-N-(4-methyl-2-thiazolylsulfonyl)amino]-4,5-dimethylphenoxymethyl]benzoic acid,
(118) 3-chloro-4-[2-[N-isopropyl-N-(4-methyl-2-thiazolylsulfonyl)amino]-4,5-dimethylphenoxymethyl]benzoic acid,
(119) 4-[2-[N-isopropyl-N-(4-methyl-2-thiazolylsulfonyl)amino]-4,5-dimethylphenoxymethyl]benzoic acid,
(120) 4-[2-[N-isobutyl-N-(4-methyl-2-thiazolylsulfonyl)amino]-4,5-dimethylphenoxymethyl]benzoic acid,
(121) 4-[2-[N-isobutyl-N-(4-methyl-2-thiazolylsulfonyl)amino]-4-chloro-5-methylphenoxymethyl]cinnamic acid,
(122) 3-methyl-4-[2-[N-isobutyl-N-(4-methyl-2-thiazolylsulfonyl)amino]-5-trifluoromethylphenoxymethyl]cinnamic acid,
(123) 3-chloro-4-[2-[N-isobutyl-N-(4-methyl-2-thiazolylsulfonyl)amino]-5-trifluoromethylphenoxymethyl]cinnamic acid,
(124) 3-methyl-4-[2-[N-isopropyl-N-(4-methyl-2-thiazolylsulfonyl)amino]-4,5-dimethylphenoxymethyl]cinnamic acid,
(125) 3-methyl-4-[2-[N-isobutyl-N-(4-methyl-2-thiazolylsulfonyl)amino]-4,5-dimethylphenoxymethyl]cinnamic acid,
(126) 4-[2-[N-isobutyl-N-(4-methyl-2-thiazolylsulfonyl)amino]-4-methyl-5-chlorophenoxymethyl]cinnamic acid,
(127) 3-methyl-4-[2-[N-isobutyl-N-(4-methyl-2-thiazolylsulfonyl)amino]-4-methyl-5-chlorophenoxymethyl]cinnamic acid,
(128) 3-methyl-4-[2-[N-isobutyl-N-(4-methyl-2-thiazolylsulfonyl)amino]-4-chloro-5-methylphenoxymethyl]cinnamic acid,
(129) N-[4-chloro-5-methyl-2-[2-methyl-4-(5-tetrazolyl)phenylmethyloxy]phenyl]-N-isobutyl-(4-methyl-2-thiazolyl)sulfonylamide,
(130) N-[4-chloro-5-methyl-2-[4-(5-tetrazolyl)phenylmethyloxy]phenyl]-N-isopropyl-(4-methyl-2-thiazolyl)sulfonylamide (hereafter, abbreviated as compound J),
(131) 4-[2-[N-isobutyl-N-(4-methyl-2-thiazolylsulfonyl)amino]-4,5-dimethylphenoxymethyl]cinnamic acid,
(132) N-[4-trifluoromethyl-2-[2-methyl-4-(5-tetrazolyl)phenylmethyloxy]phenyl]-N-isopropyl-(4-methyl-2-thiazolyl)sulfonylamide,
(133) N-[4-trifluoromethyl-2-[2-methyl-4-(5-tetrazolyl)phenylmethyloxy]phenyl]-N-isobutyl-(4-methyl-2-thiazolyl)sulfonylamide,
(134) 3-chloro-4-[2-[N-isobutyl-N-(4-methyl-2-thiazolylsulfonyl)amino]-4,5-dimethylphenoxymethyl]cinnamic acid,
(135) N-[4,5-dimethyl-2-[2-methyl-4-(5-tetrazolyl)phenylmethyloxy]phenyl]-N-isobutyl-(4-methyl-2-thiazolyl)sulfonylamide,
(136) N-[4,5-dimethyl-2-[2-methyl-4-(5-tetrazolyl)phenylmethyloxy]phenyl]-N-isopropyl-(4-methyl-2-thiazolyl)sulfonylamide,
(137) N-[4,5-dimethyl-2-[4-(5-tetrazolyl)phenylmethyloxy]phenyl]-N-isopropyl-(4-methyl-2-thiazolyl)sulfonylamide,
(138) N-[4,5-dimethyl-2-[4-(5-tetrazolyl)phenylmethyloxy]phenyl]-N-isobutyl-(4-methyl-2-thiazolyl)sulfonylamide,
(139) N-[4-chloro-5-methyl-2-[4-(5-tetrazolyl)phenylmethyloxy]phenyl]-N-isopropyl-(4-methyl-2-thiazolyl)sulfonylamide,
(140) N-[4-chloro-5-methyl-2-[4-(5-tetrazolyl)phenylmethyloxy]phenyl]-N-isobutyl-(4-methyl-2-thiazolyl)sulfonylamide,
(141) N-[4-chloro-5-methyl-2-[4-(5-oxo-1,2,4-oxadiazol-3-yl)phenylmethyloxy]phenyl]-N-isobutyl-(4-methyl-2-thiazolyl)sulfonylamide,
(142) N-[4-chloro-5-methyl-2-[2-methyl-4-(5-oxo-1,2,4-oxadiazol-3-yl)phenylmethyloxy]phenyl]-N-isobutyl-(4-methyl-2-thiazolyl)sulfonylamide,
(143) 3-methoxy-4-[2-[N-isobutyl-N-(4-methyl-2-thiazolylsulfonyl)amino]-4,5-dimethylphenoxymethyl]cinnamic acid, (144) N-[4,5-dimethyl-2-[2-methyl-4-(5-oxo-1,2,4-oxadiazol-3-yl)phenylmethyloxy]phenyl]-N-isopropyl-(4-methyl-2-thiazolyl)sulfonylamide,
(145) N-[4,5-dimethyl-2-[2-methyl-4-(5-oxo-1,2,4-oxadiazol-3-yl)phenylmethyloxy]phenyl]-N-isobutyl-(4-methyl-2-thiazolyl)sulfonylamide,
(146) N-[4,5-dimethyl-2-[4-(5-oxo-1,2,4-oxadiazol-3-yl)phenylmethyloxy]phenyl]-N-isopropyl-(4-methyl-2-thiazolyl)sulfonylamide (hereafter, abbreviated as compound L),
(147) N-[4,5-dimethyl-2-[4-(5-oxo-1,2,4-oxadiazol-3-yl)phenylmethyloxy]phenyl]-N-isobutyl-(4-methyl-2-thiazolyl)sulfonylamide,
(148) N-[4,5-dimethyl-2-[2-methoxy-4-(5-oxo-1,2,4-oxadiazol-3-yl)phenylmethyloxy]phenyl]-N-isopropyl-(4-methyl-2-thiazolyl)sulfonylamide,
(149) N-[4,5-dimethyl-2-[2-methoxy-4-(5-tetrazolyl)phenylmethyloxy]phenyl]-N-isopropyl-(4-methyl-2-thiazolyl)sulfonylamide,
(150) 4-[6-[N-isobutyl-N-(4-methyl-2-thiazolylsulfonyl)amino]indan-5-yloxymethyl]benzoic acid,
(151) 4-[6-[N-isobutyl-N-(4-methyl-2-thiazolylsulfonyl)amino]indan-5-yloxymethyl]cinnamic acid,
(152) 3-methyl-4-[6-[N-isobutyl-N-(4-methyl-2-thiazolylsulfonyl)amino]indan-5-yloxymethyl]benzoic acid,
(153) 3-methyl-4-[6-[N-isobutyl-N-(4-methyl-2-thiazolylsulfonyl)amino]indan-5-yloxymethyl]cinnamic acid,
(154) 3-methyl-4-[2-[N-(2-methyl-2-propenyl)-N-(4-methyl-2-thiazolylsulfonyl)amino]-4-chloro-5-methylphenoxymethyl]benzoic acid,
(155) 4-[2-[N-(2-methyl-2-propenyl)-N-(4-methyl-2-thiazolylsulfonyl)amino]-5-trifluoromethylphenoxymethyl]cinnamic acid,
(156) 3-methyl-4-[2-[N-(2-methyl-2-propenyl)-N-(4-methyl-2-thiazolylsulfonyl)amino]-4,5-dimethylphenoxymethyl]benzoic acid,
(157) 3-methyl-4-[6-[N-isopropyl-N-(2-thiazolylsulfonyl)amino]indan-5-yloxymethyl]benzoic acid,
(158) 3-methyl-4-[6-[N-isobutyl-N-(2-thiazolylsulfonyl)amino]indan-5-yloxymethyl]benzoic acid,
(159) 3-methyl-4-[6-[N-isopropyl-N-(4-methyl-2-thiazolylsulfonyl)amino]indan-5-yloxymethyl]benzoic acid,
(160) 4-[6-[N-isopropyl-N-(2-thiazolylsulfonyl)amino]indan-5-yloxymethyl]benzoic acid,
(161) 4-[6-[N-isobutyl-N-(2-thiazolylsulfonyl)amino]indan-5-yloxymethyl]benzoic acid,
(162) 4-[6-[N-isopropyl-N-(4-methyl-2-thiazolylsulfonyl)amino]indan-5-yloxymethyl]benzoic acid,
(163) 4-[6-[N-isopropyl-N-(4-methyl-2-thiazolylsulfonyl)amino]indan-5-yloxymethyl]cinnamic acid,
(164) 3-methyl-4-[6-[N-isopropyl-N-(4-methyl-2-thiazolylsulfonyl)amino]indan-5-yloxymethyl]cinnamic acid,
(165) 4-[2-[N-isopropyl-N-(2-thiazolylsulfonyl)amino]-4,5-dimethylphenoxymethyl]benzoic acid,
(166) 4-[2-[N-isobutyl-N-(2-thiazolylsulfonyl)amino]-4,5-dimethylphenoxymethyl]benzoic acid,
(167) 4-[2-[N-isopropyl-N-(2-thiazolylsulfonyl)amino]-4,5-dimethylphenoxymethyl]cinnamic acid,
(168) 4-[2-[N-isobutyl-N-(2-thiazolylsulfonyl)amino]-4,5-dimethylphenoxymethyl]cinnamic acid,
(169) 4-[6-[N-isopropyl-N-(2-thiazolylsulfonyl)amino]indan-5-yloxymethyl]cinnamic acid,
(170) 4-[6-[N-isobutyl-N-(2-thiazolylsulfonyl)amino]indan-5-yloxymethyl]cinnamic acid,
(171) 3-methyl-4-[2-[N-isopropyl-N-(2-thiazolylsulfonyl)amino]-4,5-dimethylphenoxymethyl]benzoic acid,
(172) 3-methyl-4-[2-[N-isobutyl-N-(2-thiazolylsulfonyl)amino]-4,5-dimethylphenoxymethyl]benzoic acid,
(173) 3-methyl-4-[2-[N-isopropyl-N-(2-thiazolylsulfonyl)amino]-4,5-dimethylphenoxymethyl]cinnamic acid,
(174) 3-methyl-4-[2-[N-isobutyl-N-(2-thiazolylsulfonyl)amino]-4,5-dimethylphenoxymethyl]cinnamic acid,
(175) 3-methyl-4-[6-[N-isopropyl-N-(2-thiazolylsulfonyl)amino]indan-5-yloxymethyl]cinnamic acid,
(176) 3-methyl-4-[6-[N-isobutyl-N-(2-thiazolylsulfonyl)amino]indan-5-yloxymethyl]cinnamic acid,
(177) 4-[3-[N-isobutyl-N-(4-methyl-2-thiazolylsulfonyl)amino]naphtharen-2-yloxymethyl]benzoic acid,
(178) 4-[3-[N-isopropyl-N-(4-methyl-2-thiazolylsulfonyl)amino]naphtharen-2-yloxymethyl]benzoic acid,
(179) 4-[3-[N-isobutyl-N-(4-methyl-2-thiazolylsulfonyl)amino]naphtharen-2-yloxymethyl]-3-methylbenzoic acid,
(180) 4-[3-[N-isopropyl-N-[2-(4-methylthiazolyl)sulfonyl]amino]naphtharen-2-yloxymethyl]-3-methylbenzoic acid,
(181) 4-[3-[N-isobutyl-N-(4-methyl-2-thiazolylsulfonyl)amino]naphtharen-2-yloxymethyl]cinnamic acid,
(182) 4-[3-[N-isopropyl-N-(4-methyl-2-thiazolylsulfonyl)amino]naphtharen-2-yloxymethyl]cinnamic acid,
(183) 4-[4,5-dimethyl-2-[N-methyl-N-(4-methyl-2-thiazolylsulfonyl)amino]phenoxymethyl]-3-methylbenzoic acid,
(184) 4-[4,5-dimethyl-2-[N-ethyl-N-(4-methyl-2-thiazolylsulfonyl)amino]phenoxymethyl]-3-methylbenzoic acid,
(185) 4-[4,5-dimethyl-2-[N-propyl-N-(4-methyl-2-thiazolylsulfonyl)amino]phenoxymethyl]-3-methylbenzoic acid,
(186) 4-[4,5-dimethyl-2-[N-(2-propenyl)-N-(4-methyl-2-thiazolylsulfonyl)amino]phenoxymethyl]-3-methylbenzoic acid,
(187) 4-[4,5-dimethyl-2-[N-cyclopropylmethyl-N-(4-methyl-2-thiazolylsulfonyl)amino]phenoxymethyl]-3-methylbenzoic acid,
(188) 4-[4,5-dimethyl-2-[N-(2-hydroxy-2-methylpropyl)-N-(4-methyl-2-thiazolylsulfonyl)amino]phenoxymethyl]-3-methylbenzoic acid,
(189) 4-[6-[N-(2-methyl-2-propenyl)-N-(4-methyl-2-thiazolylsulfonyl)amino]indan-5-yloxymethyl]benzoic acid,
(190) 4-[6-[N-(4-methyl-2-thiazolylsulfonyl)-N-(2-propenyl)amino]indan-5-yloxymethyl]benzoic acid,
(191) 4-[6-[N-cyclopropylmethyl-N-(4-methyl-2-thiazolylsulfonyl)amino]indan-5-yloxymethyl]benzoic acid,
(192) 4-[3-[N-isobutyl-N-[2-(4-methylthiazolyl)sulfonyl]amino]naphtharen-2-yloxymethyl]benzoic acid,
(193) 4-[3-[N-isopropyl-N-(4-methyl-2-thiazolylsulfonyl)amino]naphtharen-2-yloxymethyl]-3-methylbenzoic acid,
(194) 4-[6-[N-ethyl-N-(4-methyl-2-thiazolylsulfonyl)amino]indan-5-yloxymethyl]benzoic acid,
(195) 4-[6-[N-(4-methyl-2-thiazolylsulfonyl)-N-propylamino]indan-5-yloxymethyl]benzoic acid,
(196) 4-[6-[N-methyl-N-(4-methyl-2-thiazolylsulfonyl)amino]indan-5-yloxymethyl]benzoic acid,
(197) 3-methyl-4-[6-[N-methyl-N-(4-methyl-2-thiazolylsulfonyl)amino]indan-5-yloxymethyl]cinnamic acid,
(198) 4-[6-[N-ethyl-N-(4-methyl-2-thiazolylsulfonyl)amino]indan-5-yloxymethyl]-3-methylcinnamic acid,
(199) 3-methyl-4-[6-[N-(2-methyl-2-propenyl)-N-(4-methyl-2-thiazolylsulfonyl)amino]indan-5-yloxymethyl]cinnamic acid,
(200) 4-[6-[N-cyclopropylmethyl-N-(4-methyl-2-thiazolylsulfonyl)amino]indan-5-yloxymethyl]-3-methylcinnamic acid,
(201) 3-methyl-4-[6-[N-(4-methyl-2-thiazolylsulfonyl)-N-(2-propenyl)amino]indan-5-yloxymethyl]cinnamic acid, (202) 4-[6-[N-(2-hydroxy-2-methylpropyl)-N-(4-methyl-2-thiazolylsulfonyl)amino]indan-5-yloxymethyl]-3-methylcinnamic acid,
(203) 3-methyl-4-[6-[N-(4-methyl-2-thiazolylsulfonyl)-N-propylamino]indan-5-yloxymethyl]cinnamic acid,
(204) 4-[6-[N-(2-hydroxy-2-methylpropyl)-N-(4-methyl-2-thiazolylsulfonyl)amino]indan-5-yloxymethyl]benzoic acid,
(205) 4-[2-[N-isobutyl-N-(2-pyridylsulfonyl)amino]-5-trifluoromethylphenoxymethyl]cinnamic acid,
(206) 4-[2-[N-isobutyl-N-(3-pyridylsulfonyl)amino]-5-trifluoromethylphenoxymethyl]benzoic acid,
(207) 3-chloro-4-[2-[N-isopropyl-N-(2-pyridylsulfonyl)amino]-4-chloro-5-methylphenoxymethyl]benzoic acid,
(208) 3-methyl-4-[2-[N-isobutyl-N-(2-pyridylsulfonyl)amino]-4-chloro-5-methylphenoxymethyl]benzoic acid,
(209) 3-methyl-4-[2-[N-isobutyl-N-(3-pyridylsulfonyl)amino]-4-chloro-5-methylphenoxymethyl]benzoic acid,
(210) 3-methyl-4-[2-[N-isobutyl-N-(2-pyridylsulfonyl)amino]-4-methyl-5-chlorophenoxymethyl]benzoic acid,
(211) N-[4-trifluoromethyl-2-[4-(5-tetrazolyl)phenylmethyloxy]phenyl]-N-isopropyl-3-pyridylsulfonylamide,
(212) N-[4-trifluoromethyl-2-[4-(5-tetrazolyl)phenylmethyloxy]phenyl]-N-isobutyl-3-pyridylsulfonylamide,
(213) 4-[2-[N-isobutyl-N-(3-pyridylsulfonyl)amino]-4-methyl-5-chlorophenoxymethyl]benzoic acid,
(214) 3-chloro-4-[2-[N-isobutyl-N-(3-pyridylsulfonyl)amino]-4-methyl-5-chlorophenoxymethyl]benzoic acid,
(215) 3-methyl-4-[2-[N-isobutyl-N-(2-pyridylsulfonyl)amino]-5-trifluoromethylphenoxymethyl]cinnamic acid,
(216) 3-methoxy-4-[2-[N-isobutyl-N-(2-pyridylsulfonyl)amino]-4,5-dimethylphenoxymethyl]benzoic acid,
(217) 3-methoxy-4-[2-[N-isobutyl-N-(3-pyridylsulfonyl)amino]-4,5-dimethylphenoxymethyl]benzoic acid,
(218) 3-methyl-4-[2-[N-isobutyl-N-(3-pyridylsulfonyl)amino]-4,5-dimethylphenoxymethyl]benzoic acid,
(219) 3-methyl-4-[2-[N-isobutyl-N-(2-pyridylsulfonyl)amino]-4,5-dimethylphenoxymethyl]benzoic acid (hereafter, abbreviated as compound H),
(220) N-[4-trifluoromethyl-2-[4-(5-tetrazolyl)phenylmethyloxy]phenyl]-N-isopropyl-2-pyridylsulfonylamide,
(221) N-[4-trifluoromethyl-2-[4-(5-tetrazolyl)phenylmethyloxy]phenyl]-N-isobutyl-2-pyridylsulfonylamide,
(222) 3-methyl-4-[2-[N-isobutyl-N-(3-pyridylsulfonyl)amino]-4-methyl-5-chlorophenoxymethyl]benzoic acid,
(223) 4-[2-[N-isobutyl-N-(2-pyridylsulfonyl)amino]-4,5-dimethylphenoxymethyl]benzoic acid,
(224) N-[4-trifluoromethyl-2-[4-(5-oxo-1,2,4-oxadiazol-3-yl)phenylmethyloxy]phenyl]-N-isobutyl-2-pyridylsulfonylamide,
(225) 4-[2-[N-isopropyl-N-(2-pyridylsulfonyl)amino]-4-methyl-5-chlorophenoxymethyl]cinnamic acid,
(226) 3-methyl-4-[2-[N-isobutyl-N-(2-pyridylsulfonyl)amino]-4-methyl-5-chlorophenoxymethyl]cinnamic acid,
(227) 3-methyl-4-[2-[N-isobutyl-N-(2-pyridylsulfonyl)amino]-4,5-dimethylphenoxymethyl]cinnamic acid,
(228) 4-[2-[N-isobutyl-N-(3-pyridylsulfonyl)amino]-4,5-dimethylphenoxymethyl]cinnamic acid,
(229) 3-methyl-4-[2-[N-isobutyl-N-(3-pyridylsulfonyl)amino]-4,5-dimethylphenoxymethyl]cinnamic acid (hereafter, abbreviated as compound I),
(230) N-[4-trifluoromethyl-2-[2-methyl-4-(5-tetrazolyl)phenylmethyloxy]phenyl]-N-isopropyl-2-pyridylsulfonylamide,
(231) 3-chloro-4-[2-[N-isobutyl-N-(3-pyridylsulfonyl)amino]-4,5-dimethylphenoxymethyl]cinnamic acid,
(232) N-[4,5-dimethyl-2-[2-methyl-4-(5-tetrazolyl)phenylmethyloxy]phenyl]-N-isobutyl-2-pyridylsulfonylamide,
(233) N-[4,5-dimethyl-2-[2-methyl-4-(5-tetrazolyl)phenylmethyloxy]phenyl]-N-isobutyl-3-pyridylsulfonylamide,
(234) N-[4-chloro-5-methyl-2-[4-(5-tetrazolyl)phenylmethyloxy]phenyl]-N-isobutyl-3-pyridylsulfonylamide,
(235) N-[4,5-dimethyl-2-[2-chloro-4-(5-tetrazolyl)phenylmethyloxy]phenyl]-N-isobutyl-2-pyridylsulfonylamide,
(236) N-[4,5-dimethyl-2-[2-chloro-4-(5-tetrazolyl)phenylmethyloxy]phenyl]-N-isopropyl-3-pyridylsulfonylamide (hereafter, abbreviated as compound K),
(237) N-[4,5-dimethyl-2-[2-chloro-4-(5-tetrazolyl)phenylmethyloxy]phenyl]-N-isobutyl-3-pyridylsulfonylamide,
(238) 3-methyl-4-[2-[N-isobutyl-N-(3-pyridylsulfonyl)amino]-4-chloro-5-methylphenoxymethyl]cinnamic acid,
(239) N-[4,5-dimethyl-2-[4-(5-tetrazolyl)phenylmethyloxy]phenyl]-isopropyl-2-pyridylsulfonylamide,
(240) N-[4,5-dimethyl-2-[4-(5-tetrazolyl)phenylmethyloxy]phenyl]-N-isobutyl-2-pyridylsulfonylamide,
(241) N-[4,5-dimethyl-2-[4-(5-tetrazolyl)phenylmethyloxy]phenyl]-N-isobutyl-3-pyridylsulfonylamide,
(242) 3-chloro-4-[2-[N-isobutyl-N-(3-pyridylsulfonyl)amino]-5-trifluoromethylphenoxymethyl]cinnamic acid,
(243) N-[4-chloro-5-methyl-2-[2-methyl-4-(5-tetrazolyl)phenylmethyloxy]phenyl]-N-isopropyl-2-pyridylsulfonylamide,
(244) N-[4-chloro-5-methyl-2-[2-methyl-4-(5-tetrazolyl)phenylmethyloxy]phenyl]-N-isobutyl-2-pyridylsulfonylamide,
(245) N-[4,5-dimethyl-2-[2-methyl-4-(5-oxo-1,2,4-oxadiazol-3-yl)phenylmethyloxy]phenyl]-N-isopropyl-2-pyridylsulfonylamide,
(246) N-[4,5-dimethyl-2-[2-methyl-4-(5-oxo-1,2,4-oxadiazol-3-yl)phenylmethyloxy]phenyl]-N-isobutyl-3-pyridylsulfonylamide,
(247) N-[4,5-dimethyl-2-[2-methoxy-4-(5-tetrazolyl)phenylmethyloxy]phenyl]-N-isobutyl-2-pyridylsulfonylamide,
(248) N-[4,5-dimethyl-2-[2-methoxy-4-(5-tetrazolyl)phenylmethyloxy]phenyl]-N-isopropyl-2-pyridylsulfonylamide,
(249) N-[4,5-dimethyl-2-[2-methoxy-4-(5-oxo-1,2,4-oxadiazol-3-yl)phenylmethyloxy]phenyl]-N-isobutyl-2-pyridylsulfonylamide,
(250) N-[4,5-dimethyl-2-[2-methoxy-4-(5-oxo-1,2,4-oxadiazol-3-yl)phenylmethyloxy]phenyl]-N-isopropyl-2-pyridylsulfonylamide,
an alkyl ester thereof, a salt thereof, a solvate thereof or a prodrug thereof More preferable compound is 3-methyl-4-[6-[N-isobutyl-N-(2-thiazolylsulfonyl)amino]indan-5-yloxymethyl]benzoic acid (hereafter, abbreviated as compound A) and 4-[6-[N-isobutyl-N-(4-methyl-2-thiazolylsulfonyl)amino]indan-5-yloxymethyl]benzoic acid (hereafter, abbreviated as compound B), an alkyl ester thereof, a salt thereof, a solvate thereof or a prodrug thereof.

The preferable compounds of the formula (E) are the following compounds: namely, (E-1) 4-{[(5-{isobutyl[(5-methyl-2-furyl)sulfonyl]amino}-2,3-dihydro-1-benzofuran-6-yl)oxy]methyl}benzoic acid,
(E-2) 4-{[(5-{isobutyl[(4-methyl-1,3-thiazol-2-yl)sulfonyl]amino}-2,3-dihydro-1-benzofuran-6-yl)oxy]methyl}benzoic acid,
(E-3) 4-{[(5-{[(2S)-3-hydroxy-2-methylpropyl][(5-methyl-2-furyl)sulfonyl]amino}-2,3-dihydro-1-benzofuran-6-yl)oxy]methyl}benzoic acid, (E-4) 4-{[(6-{[(2R)-3-hydroxy-2-methylpropyl][(5-methyl-2-furyl)sulfonyl]amino}-2,3-dihydro-1-benzofuran-5-yl)oxy]methyl}benzoic acid,
(E-5) 4-{[(5-{(2-fluoropropyl)[(5-methyl-2-furyl)sulfonyl]amino}-2,3-dihydro-1-benzofuran-6-yl)oxy]methyl}benzoic acid,
(E-6) 4-[({6-[[(3-fluorophenyl)sulfonyl](pyridine-2-ylmethyl)amino]-2,3-dihydro-1-benzofuran-5-yl}oxy)methyl]benzoic acid,
(E-7) 4-[({6-[[(3,5-difluorophenyl)sulfonyl](pyridine-2-ylmethyl)amino]-2,3-dihydro-1-benzofuran-5-yl}oxy)methyl]benzoic acid,
(E-8) N-isobutyl-5-methyl-N-(6-{[4-(5-oxo-4,5-dihydro-1,2,4-oxadiazol-3-yl)benzyl]oxy}-2,3-dihydro-1-benzofuran-5-yl)furan-2-sulfonamide,
(E-9) 4-{[(6-{isobutyl[(4-methyl-1,3-thiazol-2-yl)sulfonyl]amino}-2,3-dihydro-1-benzofuran-5-yl)oxy]methyl}benzoic acid,
(E-10) 4-[({6-[[(4-methyl-1,3-thiazol-2-yl)sulfonyl](pyridine-2-ylmethyl)amino]-2,3-dihydro-1-benzofuran-5-yl}oxy)methyl]benzoic acid,
(E-11) 5-{[(5-{isobutyl[(5-methyl-2-furyl)sulfonyl]amino}-2,3-dihydro-1-benzofuran-6-yl)oxy]methyl}thiophene-2-carboxylic acid,
(E-12) 3-chloro-4-{[(5-{isobutyl[(4-methyl-1,3-thiazol-2-yl)sulfonyl]amino}-2,3-dihydro-1-benzofuran-6-yl)oxy]methyl}benzoic acid,
(E-13) 4-{[(5-{isobutyl[(5-methyl-2-furyl)sulfonyl]amino}-2,3-dihydro-1-benzothien-6-yl)oxy]methyl}benzoic acid,
(E-14) 5-{[(5-{isobutyl[(4-methyl-1,3-thiazol-2-yl)sulfonyl]amino}-2,3-dihydro-1-benzofuran-6-yl)oxy]methyl}thiophene-2-carboxylic acid,
(E-15) 4-[({5-[[(5-methyl-2-furyl)sulfonyl](pyridine-2-ylmethyl)amino]-2,3-dihydro-1-benzothien-6-yl}oxy)methyl]benzoic acid,
(E-16) 4-{[(5-{isobutyl[(5-methyl-2-furyl)sulfonyl]amino}-1,1-dioxide-2,3-dihydro-1-benzothien-6-yl)oxy]methyl}benzoic acid, the compounds of working example 1 to 516 disclosed in the tables 19 to 82 of WO2006/121097 (represented by the number on column "Ex" in the tables), the compound disclosed in the table 83 of the patent document, an alkyl ester thereof, a salt thereof, a solvate thereof or a prodrug thereof.

The preferable compounds of the formula (G) are the following compounds: namely,
(G-1) 4-[({6-[[(4-methyl-1,3-thiazol-2-yl)sulfonyl](oxetane-2-ylmethyl)amino]-2,3-dihydro-1H-indan-5-yl}oxy)methyl]benzoic acid,
(G-2) 4-{[(6-{[(3-methyloxetane-3-yl)methyl][(4-methyl-1,3-thiazol-2-yl)sulfonyl]amino}-2,3-dihydro-1H-indan-5-yl)oxy]methyl}benzoic acid,
(G-3) 4-[({6-[[(3,5-difluorophenyl)sulfonyl](oxetane-2-ylmethyl)amino]-2,3-dihydro-1H-indan-5-yl}oxy)methyl]benzoic acid,
(G-4) 4-[({6-[[(4-methyl-1,3-thiazol-2-yl)sulfonyl](pyridine-2-ylmethyl)amino]-2,3-dihydro-1H-indan-5-yl}oxy)methyl]benzoic acid,
(G-5) 4-[({6-[[(4-methyl-1,3-thiazol-2-yl)sulfonyl](tetrahydrofuran-3-ylmethyl)amino]-2,3-dihydro-1H-indan-5-yl}oxy)methyl]benzoic acid,
(G-6) 4-[({6-[[(5-methyl-2-furyl)sulfonyl](tetrahydrofuran-3-ylmethyl)amino]-2,3-dihydro-1H-indan-5-yl}oxy)methyl]benzoic acid,
(G-7) 4-[({6-[(pyridine-2-ylmethyl)(pyridine-3-ylsulfonyl)amino]-2,3-dihydro-1H-indan-5-yl}oxy)methyl]benzoic acid,
(G-8) 4-({4,5-dimethyl-2-[[(4-methyl-1,3-thiazol-2-yl)sulfonyl](pyridine-2-ylmethyl)amino]phenoxy}methyl)benzoic acid,
(G-9) 4-({4-chloro-5-methyl-2-[[(4-methyl-1,3-thiazol-2-yl)sulfonyl](pyridine-2-ylmethyl)amino]phenoxy}methyl)benzoic acid,
(G-10) 4-{[2-[[(4-methyl-1,3-thiazol-2-yl)sulfonyl](pyridine-2-ylmethyl)amino]-5-(trifluoromethyl)phenoxy]methyl}benzoic acid,
(G-11) 4-({4,5-dimethyl-2-[(pyridine-2-ylmethyl)(pyridine-3-ylsulfonyl)amino]phenoxy}methyl)benzoic acid,
(G-12) 4-{[(6-{[(1-methyl-1H-pyrazole-4-yl)methyl][(4-methyl-1,3-thiazol-2-yl)sulfonyl]amino}-2,3-dihydro-1H-indan-5-yl)oxy]methyl}benzoic acid,
(G-13) 4-({5-methoxy-4-methyl-2-[[(4-methyl-1,3-thiazol-2-yl)sulfonyl](pyridine-2-ylmethyl)amino]phenoxy}methyl)benzoic acid,
(G-14) 4-({4,5-dimethyl-2-[(pyridine-2-ylmethyl)(pyridine-2-ylsulfonyl)amino]phenoxy}methyl)benzoic acid,
4-[({6-[[(2-fluorophenyl)sulfonyl](pyridine-2-ylmethyl)amino]-2,3-dihydro-1H-indan-5-yl}oxy)methyl]benzoic acid,
(G-15) 4-{[(6-{[(1-methyl-1H-imidazole-2-yl)methyl][(4-methyl-1,3-thiazol-2-yl)sulfonyl]amino}-2,3-dihydro-1H-indan-5-yl)oxy]methyl}benzoic acid, the compounds of working example 1 to 4, 153 and 165 disclosed in WO2007/072782,
the compounds disclosed in the table 8 to 24 of such patent document,
an alkyl ester thereof, a salt thereof, a solvate thereof or a prodrug thereof.

WO2003/101959, WO2006/114272 and WO2007/113289 can be cited as the other EP1 antagonists.

In the present invention, unless otherwise indicated and as is apparent for those skilled in the art, the symbol ⦀ indicates that it is bound to the opposite side of the sheet (namely α-configuration); the symbol ⧸ indicates that it is bound to the front side of the sheet (namely β-configuration); and the symbol ⧸ indicates that it is a α-configuration, β-configuration or a mixture thereof.

Unless otherwise specified, all isomers are included in the compounds represented by the formula (A), (B), (E), (G) and (I). For example, an alkyl, alkenyl, alkynyl, alkoxy, alkylthio, alkylene, alkenylene and alkynylene group mean straight-chain or branched-chain ones. In addition, isomers on a double bond, a ring, a fused ring (E-, Z-, cis-, trans-isomer), isomers generated from asymmetric carbon atom(s) (R—, S-isomer, α-, β-configuration, enantiomer, diastereomer), optically active isomers (D-, L-, d-, l-isomer), polar compounds generated by chromatographic separation (more polar compound, less polar compound), equilibrium compounds, rotational isomers, mixtures thereof at voluntary ratios and racemic mixtures are also included in the compounds represented by the formula (A), (B), (E), (G) and (I).

When the compounds represented by the formula (A), (B), (E), (G) and (I) have a carboxy group, these compounds may be converted into the corresponding ester by methods known per se. The conversion into ester is useful since it increases stability and absorbability of the compound. In the present description, preferred alkyl ester is C1-6 alkyl ester (e.g., methyl ester, ethyl ester, n-propyl ester, isopropyl ester, n-butyl ester, isobutyl ester, sec-butyl ester, tert-butyl ester, n-pentyl ester, n-hexyl ester and so forth) and more preferred alkyl ester is C1-4 alkyl ester (e.g., methyl ester, ethyl ester, n-propyl ester, isopropyl ester, n-butyl ester, isobutyl ester and so forth).

A salt of the compound represented by the formula (A), (E) and (G), a salt of an alkylester of such compound, and a salt of the compound represented by the formula (B) and (I) are all preferable. And more preferred salt is water-soluble one. A suitable salt includes, for example, a salt of alkaline metal (e.g., potassium, sodium and so forth), a salt of alkaline earth metal (e.g., calcium, magnesium and so forth), an ammonium salt, a salt of pharmaceutically acceptable organic amine (e.g., tetramethylammonium, triethylamine, methylamine, dimethylamine, cyclopentylamine, benzylamine, phenethylamine, piperidine, monoethanolamine, diethanolamine, tris (hydroxymethyl)aminomethane, lysine, arginine, N-methyl-D-glucamine and so forth). A suitable acid addition salt includes, for example, an inorganic acid salt such as hydrochloride, hydrobromide, hydroiodide, sulfate, phosphate, nitrate and so forth or an organic acid salt such as acetate, lactate, tartrate, benzoate, citrate, methanesulfonate, ethanesulfonate, benzene sulfonate, toluene sulfonate, isethionate, glucuronate, gluconate and so forth. The acid addition salt is preferably water-soluble one.

The compound represented by the formula (A), (E) and (G), an alkylester thereof or a salt thereof and the compound represented by the formula (B) and (I) or a salt thereof may be converted into the corresponding solvate. A non-toxic and water-soluble solvate is preferable. A suitable solvate includes, for example, a solvate of water or alcohols solvent (e.g., ethanol and so forth).

The compound represented by the formula (A), (E) and (G), an alkylester thereof or a salt thereof and the compound represented by the formula (B) and (I), a salt thereof or a solvate thereof may be converted into the corresponding cyclodextrin clathrates by the method described in JP50003362B, JP52031404B or JP61052146B using α-, β- or γ-cyclodextrin or a mixture thereof. By converting into the corresponding cyclodextrin clathrates, the stability and solubility in water of the compounds increase, and therefore it is useful in the use for pharmaceuticals.

A prodrug of the compound represented by the formula (A), (E) and (G), an alkylester thereof or a salt thereof and the compound represented by the formula (B) and (I), a salt thereof or a solvate thereof means a compound converted into the compound represented by the formula (A), (E) and (G), an alkylester thereof, a salt thereof, the compound represented by the formula (B) and (I), a salt thereof or a solvate thereof by the reaction with enzymes, gastric acids and so on in vivo. The prodrugs include, when the compounds represented by the formula (A), (B), (E), (G) and (I) have an amino group, the compound wherein the amino group of the compound is acylated, alkylated or phosphorylated (e.g., the compound wherein the amino group of the compound represented by the formula (A), (B), (E), (G) and (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, and so forth); when the compounds represented by the formula (A), (B), (E), (G) and (I) have hydroxy group, the compound wherein the hydroxy group of the compound is acylated, alkylated, phosphorylated or borated (e.g., the compound wherein the hydroxy group of the compound represented by the formula (A), (B), (E), (G) and (I) is acetylated, palmitoylated, propanoylated, pivaloylated, succinylated, fumarylated, alanylated, dimethylaminomethylcarbonylated and so forth); when the compounds represented by the formula (A), (B), (E), (G) and (I) have carboxyl group, the compound wherein the carboxyl group of the compound is esterified or amidated (e.g., the compound wherein the carboxyl group of the compound represented by the formula (A), (B), (E), (G) and (I) is converted into an ester such as ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, or the compounds wherein the carboxyl group is methylamidated) and so on. These compounds can be prepared by methods known per se and may be any one of hydrates and non-hydrates. And these prodrugs may be converted into the compound represented by the formula (A), (E) and (G), an alkylester thereof or a salt thereof and the compound represented by the formula (B) and (I), a salt thereof or a solvate thereof under physiological conditions as described in "*Iyakuhin no Kaihatsu*", Vol. 7, "Bunshi Sekkei", pp. 163-198 (Hirokawa Shoten, 1990).

In addition, the compound represented by the formula (A), (E) and (G), an alkylester thereof or a salt thereof and the compound represented by the formula (B) and (I), a salt thereof or a solvate thereof may be labeled with an isotope (e.g., $^3H$, $^{14}C$, $^{35}S$, $^{125}I$, etc.) and so on.

Processes for the Preparation of the Compounds Involved in the Present Invention The compound represented by the formula (A), (E) and (G), an alkylester thereof or a salt thereof and the compound represented by the formula (B) and (I), a salt thereof or a solvate thereof can be prepared by the methods described in Japanese Patent No. 3426252, EP878465, Japanese Patent No. 3741120, WO2006/121097 and WO2007/113289, the known methods described in, for example, JP52027753, JP55100360, WO2003/074483, Synlett 2002, No. 1, 239-242 or Comprehensive Organic Transformations: A Guide to Functional Group Preparations, 2nd Edition (Richard C. Larock, John Wiley & Sons Inc, 1999), an appropriately improved method or a combined method thereof. The other EP1 antagonists can be prepared by the processes for the preparation described in corresponding documents or patent documents.

Toxicity

It has been confirmed that the EP1 antagonists involved in the present invention has low toxicity and is sufficiently safe for use as a pharmaceutical preparation.

Application for Pharmaceuticals

The EP1 antagonist involved in the present invention is effective for prevention, treatment and/or symptom improvement of a dysuria (e.g., slow stream, splitting or spraying of the urine stream, intermittent stream, hesitancy, straining to void, terminal dribble and so forth).

The EP1 antagonist involved in the present invention may be administered in combination with other medicaments for the purpose of (1) complement and/or enhancement of the effect of prevention, treatment and/or symptom improvement, (2) improvement of dynamics and absorption, lowering of dosage and/or (3) alleviation of side effect.

The combination of the $EP_1$ antagonist involved in the present invention and other medicaments may be administered as a composition in one drug product comprising these components, or may be administered separately. In the case of the separated administration, they may be administered simultaneously or with time lag. Administration with time lag includes the method of firstly administering the agent of the present invention and subsequently administering other drugs, and the method of firstly administering the other drug and subsequently administering the agent of the present invention, and they may be administered in the same route or not.

The other medicaments which compensate and/or enhance the effect of the prevention, treatment and/or symptom improvement of a dysuria by using the $EP_1$ antagonist involved in the present invention include, for example, an acetylcholinesterase inhibitor (e.g., distigmine, neostigmine and so forth) or an α1 receptor antagonist (e.g., tamsulosin, prazosin, alfuzosin, naftopidil, urapidil and so forth).

The weight proportion of the $EP_1$ antagonist involved in the present invention and other medicaments is not limited in particular. Arbitrary two or more of the other medicaments may be administered in combination.

Based on the above-described mechanism, the other medicaments which compensate and/or enhance the effect of prevention, treatment and/or symptom improvement of a dysuria by using the $EP_1$ antagonist involved in the present invention include not only those which have so far been found but also those which will be found on the basis of the aforementioned mechanism.

To use the combination of the $EP_1$ antagonist involved in the present invention and the other medicaments for the above-described purposes, they are usually administered systemically or topically in the form of oral or parenteral administration.

The dosages of the $EP_1$ antagonist involved in the present invention varies depending on age, body weight, symptom, therapeutic effect, administration route and treatment time as the compounds vary per se. Generally, the dosages per person per administration to an adult human are from 1 ng to 100 mg up to several times per day by oral administration. Alternatively, they are from 0.1 ng to 10 mg up to several times per day by parenteral administration or they are administrated into vein continuously for from 1 to 24 hours per day.

As mentioned above, the dosage depends upon various conditions, and thus there are cases in which doses lower than the range as specified above may be enough or doses greater than the range as specified above may be required.

The $EP_1$ antagonist involved in the present invention or a combination of the $EP_1$ antagonist involved in the present invention and the other medicaments may be administered in the composition of, for example, solid compositions or liquid compositions for oral administration, or injections, external preparations, suppositories, eye drops or inhalants, each of which are for parenteral administration.

The solid compositions for oral administration include tablets, pills, capsules, dispersible powders and granules, etc. The capsules include hard capsules and soft capsules.

In such solid compositions for oral use, one or more active compound(s) are admixed solely or with an excipient (e.g., lactose, mannitol, glucose, microcrystalline cellulose, starch and so forth), a binder (e.g., hydroxypropylcellulose, polyvinylpyrrolidone, magnesium metasilicate aluminate and so forth), a disintegrating agent (e.g., calcium cellulose glycolate and so forth), a lubricant (e.g., magnesium stearate and so forth), a stabilizer and a dissolution aid (e.g., glutamic acid, aspartic acid and so forth), and then formulated into a preparation in the conventional manner. If necessary, such preparations may be coated with a coating agent (e.g., sucrose, gelatin, hydroxypropylcellulose, hydroxypropylmethylcellulose phthalate and so forth) or they may be coated with two or more coating layers. Furthermore, the solid compositions for oral use include capsules of absorbable materials like gelatin.

The liquid compositions for oral administration include pharmaceutically acceptable solutions, suspensions, emulsions, syrups and elixirs, etc. In such liquid compositions, one or more of the active compound(s) may be dissolved, suspended or emulized into diluent(s) commonly used in the art (e.g., purified water, ethanol or a mixture thereof and so forth). Besides such diluents, said compositions may also contain some additives, such as wetting agents, suspending agents, emulsifying agents, sweetening agents, flavoring agents, aroma, preservative or buffering agents.

The external preparations for parenteral administration include, for example, ointments, gels, creams, poultices, patches, liniments, atomized agents, inhalations and sprays, etc. They include one or more active compound(s) and are prepared by methods known per se or by conventional methods.

The ointments are prepared by methods known per se or by conventional methods. For example, they are prepared by levigation or fusion of one or more active compound(s) and substrate. The substrate for the ointment is selected from known or usual one. It includes, for example, a higher fatty acid or a higher fatty acid ester (e.g., adipic acid, myristic acid, palmitic acid, stearic acid, oleic acid, adipic acid ester, myristic acid ester, palmitic acid ester, stearic acid ester, oleic acid ester and so forth), a wax (e.g., yellow beeswax, spermaceti, ceresin and so forth), a surfactant (e.g., polyoxyethylene alkyl ether phosphoric acid ester and so forth), a higher alcohol (e.g., cetanol, stearil alcohol, cetostearyl alcohol and so forth), a silicon oil (e.g., dimethyl polysiloxane and so forth), a hydrocarbon (e.g., hydrophilic petrolatum, white petrolatum, purified lanolin, liquid paraffin and so forth), a glycol (e.g., ethylene glycol, diethylene glycol, propylene glycol, polyethylene glycol, macrogol and so forth), a vegetable oil (e.g., castor oil, olive oil, sesame oil, turpentine oil and so forth), an animal oil (e.g., mink oil, egg yolk oil, squalane, squalene and so forth), water, an absorption accelerator and an irritation inhibitor. These substrates are used independently or as mixture of two or more. Moreover, humectants, preservative agents, stabilizers, antioxidative agents, fragrant materials, etc. may be contained.

The gels are prepared by methods known per se or by conventional methods. For example, they are prepared by fusion of one or more active compound(s) and substrate. The substrate for the gel is selected from known or usual one. It includes, for example, a lower alcohol (e.g., ethanol, isopropylalcohol and so forth), a gelling agent (e.g., carboxy methyl cellulose, hydroxy ethyl cellulose, hydroxy propyl cellulose, ethyl cellulose and so forth), a neutralizing agent (e.g., triethanolamine, diisopropanolamine and so forth), a surfactant (e.g., polyethylene glycol monostearate and so forth), a gum, water, an absorption accelerator and an irritation inhibitor. These substrates are used independently or as mixture of two or more. Moreover, preservative agents, antioxidative agents, fragrant materials, etc. may be contained.

The creams are prepared by methods known per se or by conventional methods. For example, they are prepared by fusion or emulsification of one or more active compound(s) and substrate. The substrate for the cream is selected from known or usual one. It includes, for example, a higher fatty acid ester, a lower alcohol, a hydrocarbon, a polyalcohol (e.g., propylene glycol, 1,3-butylene glycol and so forth), a higher alcohol (e.g., 2-hexyldecanol, cetanol and so forth), an emulsifying agent (e.g., polyoxyethylene alkyl ether, fatty acid ester and so forth), water, an absorption accelerator and an irritation inhibitor. These substrates are used independently or as mixture of two or more. Moreover, preservative agents, antioxidative agents, fragrant materials, etc. may be contained.

The poultices are prepared by methods known per se or by conventional methods. For example, they are prepared by fusion of one or more active compound(s) and substrate, and then the kneaded one is laid over support medium. The substrate for the poultice is selected from known or usual one. It includes, for example, a thickening agent (e.g., polyacrylic acid, polyvinylpyrolidone, gum acacia, starch, gelatin, methyl cellulose and so forth), a wetting agent (e.g., urea, glycerin, propylenegrycol and so forth), a bulking agent (e.g., kaolin, zinc oxide, talc, calcium, magnesium and so forth), water, a solubilizing agent, a thickener and an irritation inhibitor. These substrates are used independently or as mixture of two or more. Moreover, preservative agents, antioxidative agents, fragrant materials, etc. may be contained.

The patches are prepared by methods known per se or by conventional methods. For example, they are prepared by fusion of one or more active compound(s) and substrate, and then laid over support medium. The substrate for the patch is selected from known or usual one. It includes, for example, a polymer substrate, a fat, a higher fatty acid, a thickener and an irritation inhibitor. These substrates are used independently or as mixture of two or more. Moreover, preservative agents, antioxidative agents, fragrant materials, etc. may be contained.

The liniments are prepared by methods known per se or by conventional methods. For example, they are prepared by dissolving, suspending or emulsifying one or more active compound(s) in one or more selected from water, alcohol (e.g., ethanol, polyethylene glycol and so forth), a higher fatty acid, a glycerin, a soap, a emulsifying agent, a suspending agent, etc. The liniments may further contain preservative agents, antioxidative agents, fragrant materials, etc.

The atomized agents, inhalations and sprays may comprise, in addition to a diluent commonly employed, a stabilizer such as sodium bisulfite and a buffer for imparting isotonicity, for example, an isotonic agent such as sodium chloride, sodium citrate or citric acid.

The injections for parenteral administration include solutions, suspensions, emulsions and solid forms which are dissolved or suspended into a solvent for injection before use. Such injections are used by dissolving, suspending or emulsifying one or more active compound(s) in a solvent. The solvents include, for example, distilled water for injection, physiological salt solution, vegetable oil, propylene glycol, polyethylene glycol, alcohol such as ethanol, or a mixture thereof. The injections may further comprise some additives, such as stabilizing agents, solution adjuvants (e.g., glutamic acid, aspartic acid, POLYSORBATE80 (registered trade mark) and so forth), suspending agents, emulsifying agents, soothing agents, buffering agents, preservatives, and the like. Such injections may be produced by sterilizing at a final step, or may be prepared by an aseptic manipulation. Alternatively, it may be also manufactured in the form of sterile solid forms, for example, freeze-dried products, which may be dissolved in sterile water or some other sterile diluent(s) for injection before use.

The inhalants for parenteral administration include aerosol, powders for inhalation or liquids for inhalation. The liquids for inhalation may be dissolved or suspended in water or the other appropriate solvent before use. Such inhalants are prepared by methods known per se. For example, the liquids for inhalation are prepared by using appropriate additives such as an antiseptic (e.g., benzalkonium chloride, para-hydroxybenzoic acid ester and so forth), a coloring agent, a buffering agent (e.g., sodium phosphate, sodium acetate and so forth), an isotonizing agent (e.g., sodium chloride, concentrated glycerin and so forth), a thickening agent (e.g., carboxyvinylpolymer and so forth), or an accelerator of absorption, etc., if necessary.

The powders for inhalation are prepared by using appropriate additives such as a lubricant agent (e.g., stearin acid and the salt thereof and so forth), a binding agent (e.g., starch, dextrin and so forth), a diluting agent (e.g., lactose, cellulose and so forth), a coloring agent, an antiseptic (e.g., benzalkonium chloride, para-hydroxybenzoic acid ester and so forth), an accelerator of absorption, etc., if necessary.

In cases where the liquids for inhalation are administered, a spray (e.g., atomizer, nebulizer) is usually used, and in cases where the powders for inhalation are administered, an inhalation administration apparatus for powder agents is usually used.

The other compositions for parenteral administration include suppositories for intrarectal administration and pessaries for vaginal administration, each of which comprise one or more of the active substance(s) and are prepared by methods known per se.

EXAMPLES

Hereinafter, although the present invention is detailed by examples and formulation examples, the present invention is not limited thereto. In the following examples, various conditions can be changed within the range in which it doesn't deviate from the range of this invention. Conventional methods based on the basic biological techniques are used for various operations of the following examples.

Example 1

Measurement of EP1 Antagonist Activity

The cells expressing mouse EP1 receptor were seeded at $10^4$ cells/well in 96-well plates and cultured for 2 days with 10% Fetal Bovine Serum (FBS)/alpha Modified Eagle Medium ($\alpha$MEM) in the incubator (37° C., 5% $CO_2$). The cells were washed with phosphate buffer, and load buffer (10% FBS/$\alpha$MEM containing Fura2/AM (5 $\mu$M), indomethacin (20 $\mu$M) and probenecid (2.5 mM)) was then added to each well and cells were left standing for 1 hour. Load buffer of each well was discarded and assay buffer (Hank's Balanced Salt Solution (HBSS) containing indomethacin (2.5 mM), probenecid (2.5 mM), HEPES-NaOH (10 mM) and 0.1% (w/v) Bovine Serum Albumin (BSA)) was added to each well and plates were left at room temperature in a dark room for 1 hour. Afterwards, compounds of the present invention (10 $\mu$L) or $PGE_2$ (10 $\mu$L) prepared with assay buffer was added to each well and intracellular calcium concentrations were measured using a Fluorescence Drug Screening System (FDSS-4000, Hamamatsu Photonics K.K.). Changes in ratio of fluorescent intensity at 500 nm in cells exposed to alternating 2 excitation wavelengths was monitored as changes in intracellular calcium concentrations.

$IC_{50}$ values were calculated based on the response inhibition rate of increase in intracellular calcium concentrations induced by PGE2 (100 nM) and was used as an index of EP1 antagonistic activity. The results are shown in following Table 1.

TABLE 1

| Compounds | $IC_{50}(\mu M)$ |
|---|---|
| Compound A | 0.0069 |
| Compound B | 0.0093 |
| Compound C | 0.0078 |
| Compound D | 0.0072 |

TABLE 1-continued

| Compounds | IC$_{50}$(μM) |
|---|---|
| Compound E | 0.021 |
| Compound F | 0.0041 |
| Compound G | 0.025 |
| Compound H | 0.0073 |
| Compound I | 0.0092 |
| Compound J | 0.0049 |
| Compound K | 0.0037 |
| Compound L | 0.0071 |

Example 2

Evaluation in Animal Model of Dysuria Induced by Intravesical Infusion of Adenosine Triphosphate (Hereinafter, Abbreviated as ATP)

After administration of ketamine hydrochloride anesthesia (15 to 20 mg/kg), male cynomolgus monkeys (11 years, 3 male (symbol "○" in the FIG. 1 and FIG. 2 represents individual one.)) were fixed onto a stereotaxic operating table. The top of the bladder catheter was connected to a pressure transducer via a three-way stopcock, and intravesical pressure was recorded using a distortion amplifier and a recorder. The other end of the three-way stopcock were connected to a syringe for intravesical infusion to which an infusion pump was connected and a extension tube which satisfied physiological saline to remove residual urine from bladder.

The physiological saline was infused into the bladder at an infusion rate of 1.5 to 7.0 mL/min, and immediately after completion of voiding, the intravesical infusion was terminated and residual urine was removed (hereinafter, the above procedures is assumed singlecystometry.) and the procedures were repeated. After repeating singlecystometry by the physiological saline twice or more, singlecystometry with ATP solution (0.01 to 1.0 mmol/L) was repeated twice or more. And after subcutaneous administration of the compound A (0.1 mg/1 mL/kg), singlecystometry was conducted using ATP solution. Urinary flow rate (voided volume per voiding time (mL/sec)) and residual urine rate (residual urine volume per voided volume (%)) were calculated for each of the singlecystometry before ATP perfusion, after ATP perfusion and after ATP perfusion conducted after administration of the compound A. The results are shown in FIG. 1 and FIG. 2.

The compound A recovered the urinary flow rate decreased by ATP, and decreased the residual urine rate.

Formulation Example 1

3-methyl-4-[6-[N-isobutyl-N-(2-thiazolylsulfonyl) amino]indan-5-yloxymethyl]benzoic acid (5.0 g), calcium carboxymethylcellulose (20 g), magnesium stearate (10 g) and microcrystalline cellulose (920 g) were admixed in a conventional method and punched out to give 10,000 tablets each containing 0.5 mg of active ingredient.

Formulation Example 2

3-methyl-4-[6-[N-isobutyl-N-(2-thiazolylsulfonyl) amino]indan-5-yloxymethyl]benzoic acid (2.0 g), Mannit (500 g) and distilled water (10 L) were admixed in a conventional method and solution is sterilizated in a conventional method, followed by filling into vials each containing 1 ml and lyophilizing in a conventional method to obtain 10,000 vials each containing 0.2 mg of active ingredient.

INDUSTRIAL APPLICABILITY

EP$_1$ antagonist of the present invention is effective for prevention, treatment and/or symptom improvement of a dysuria (e.g., slow stream, splitting or spraying of the urine stream, intermittent stream, hesitancy, straining to void, terminal dribble).

Figure 1:
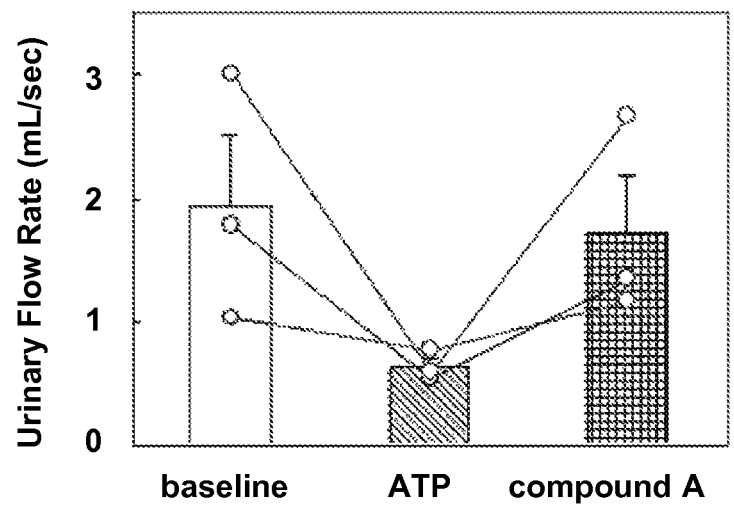
FIG. 1 shows urinary flow rate (mL/sec) before ATP perfusion (baseline), after ATP perfusion (ATP) and after ATP perfusion conducted after administration of the compound A (compound A).
Figure 2:
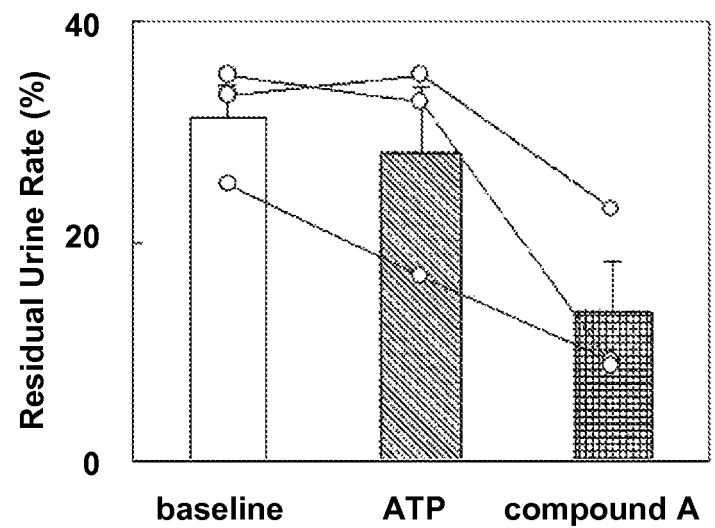
FIG. 2 shows residual urine rate (%) before ATP perfusion (baseline), after ATP perfusion (ATP) and after ATP perfusion conducted after administration of the compound A (compound A).

The invention claimed is:

1. A method for increasing urinary flow rate in a dysuria patient with one or more urinary symptoms selected from the group consisting of slow stream, splitting or spraying of the urine stream, intermittent stream, hesitancy, straining to void, and terminal dribble, said method comprising administering an effective amount of 3-methyl-4-[6-[N-isobutyl-N-(2-thiazolylsulfonyl)-amino]indan-5-yloxymethyl]-benzoic acid or a salt thereof to said dysuria patient.

2. The method according to claim 1, wherein the administration of 3-methyl-4-[6-[N-isobutyl-N-(2-thiazolylsulfonyl)-amino]indan-5-yloxymethyl]-benzoic acid or a salt thereof has a contractile action on detrusor muscle, and a weakening action on bladder outlet resistance, in said dysuria patient.

3. The method according to claim 1, wherein said administration decreases said dysuria patient's residual urine rate.

4. A method for increasing urinary flow rate of a dysuria patient in need of an increase in urinary flow rate, said method comprising administering an effective amount of 3-methyl-4-[6-[N-isobutyl-N-(2-thiazolylsulfonyl)amino]indan-5-yloxymethyl]-benzoic acid or a salt thereof to said dysuria patient, and wherein said dysuria patient has one or more urinary symptoms selected from the group consisting of slow stream, splitting or spraying of the urine stream, intermittent stream, hesitancy, straining to void and terminal dribble.

5. A method for treating and/or improving one or more urinary symptoms in a dysuria patient, said one or more urinary symptoms being selected from the group consisting of slow stream, splitting or spraying of the urine stream, intermittent stream, hesitancy, straining to void and terminal dribble, said method comprising administering an effective amount of 3-methyl-4-[6-[N-isobutyl-N-(2-thiazolylsulfonyl)amino]indan-5-yloxymethyl]-benzoic acid or a salt thereof to said dysuria patient, to thereby increase urinary flow rate and/or decrease residual urine rate.

* * * * *